US00RE42226E

(19) United States
(12) Reissued Patent
Foley et al.

(10) Patent Number: US RE42,226 E
(45) Date of Reissued Patent: *Mar. 15, 2011

(54) PERCUTANEOUS REGISTRATION APPARATUS AND METHOD FOR USE IN COMPUTER-ASSISTED SURGICAL NAVIGATION

(75) Inventors: Kevin T Foley, Germantown, TN (US); John B Clayton, Superior, CO (US); Anthony Melkent, Memphis, TN (US); Michael C Sherman, Memphis, TN (US)

(73) Assignee: Medtronic Navigation, Inc., Louisville, CO (US)

( * ) Notice: This patent is subject to a terminal disclaimer.

(21) Appl. No.: 11/451,595

(22) Filed: Jun. 12, 2006

Related U.S. Patent Documents

Reissue of:
(64) Patent No.: 6,226,548
Issued: May 1, 2001
Appl. No.: 09/148,498
Filed: Sep. 4, 1998

U.S. Applications:
(

(63) Continuation of application No. 10/423,332, filed on Apr. 24, 2003, now Pat. No. Re. 39,133
(60) Provisional application No. 60/059,915, filed on Sep. 24, 1997.

(51) Int. Cl.
*A61B 5/05* (2006.01)

(52) U.S. Cl. ..... 600/426
(58) Field of Classification Search ..... 600/407, 600/426, 427, 429, 414, 417; 606/60, 61, 606/65, 104, 130; 604/236; 623/1.34
See application file for complete search history.

(56) References Cited

U.S. PATENT DOCUMENTS

| | | | |
|---|---|---|---|
| 1,576,781 | A | 3/1926 | Phillips |
| 1,735,726 | A | 11/1929 | Bornhardt |
| 2,407,845 | A | 9/1946 | Nemeyer |
| 2,650,588 | A | 9/1953 | Drew |
| 2,697,433 | A | 12/1954 | Sehnder |
| 3,016,899 | A | 1/1962 | Stenvall |
| 3,017,887 | A | 1/1962 | Heyer |
| 3,061,936 | A | 11/1962 | Dobbeleer |
| 3,073,310 | A | 1/1963 | Mocarski |

(Continued)

FOREIGN PATENT DOCUMENTS

| | | |
|---|---|---|
| CA | 964149 | 3/1975 |

(Continued)

OTHER PUBLICATIONS

Office Action mailed Dec. 12, 2008 in pending U.S. Appl. No. 11/451,594, filed Jun. 12, 2006.

(Continued)

*Primary Examiner*—George Manuel
(74) *Attorney, Agent, or Firm*—Harness, Dickey, Pierce, P.L.C.

(57) ABSTRACT

An apparatus and procedures for percutaneous placement of surgical implants and instruments such as, for example, screws, rods, wires and plates into various body parts using image guided surgery. The invention includes an apparatus for use with a surgical navigation system, an attaching device rigidly connected to a body part, such as the spinous process of a vertebrae, with an identification superstructure rigidly but removably connected to the attaching device. This identification superstructure, for example, is a reference arc and fiducial array which accomplishes the function of identifying the location of the superstructure, and, therefore, the body part to which it is fixed, during imaging by CAT scan or MRI, and later during medical procedures.

53 Claims, 19 Drawing Sheets

U.S. PATENT DOCUMENTS

| | | | |
|---|---|---|---|
| 3,109,588 | A | 11/1963 | Polhemus et al. |
| 3,294,083 | A | 12/1966 | Alderson |
| 3,367,326 | A | 2/1968 | Frazier |
| 3,439,256 | A | 4/1969 | Kähne et al. |
| 3,577,160 | A | 5/1971 | White |
| 3,614,950 | A | 10/1971 | Rabey |
| 3,644,825 | A | 2/1972 | Davis, Jr. et al. |
| 3,674,014 | A | 7/1972 | Tillander |
| 3,702,935 | A | 11/1972 | Carey et al. |
| 3,704,707 | A | 12/1972 | Halloran |
| 3,821,469 | A | 6/1974 | Whetstone et al. |
| 3,868,565 | A | 2/1975 | Kuipers |
| 3,941,127 | A | 3/1976 | Froning |
| 3,983,474 | A | 9/1976 | Kuipers |
| 4,017,858 | A | 4/1977 | Kuipers |
| 4,037,592 | A | 7/1977 | Kronner |
| 4,052,620 | A | 10/1977 | Brunnett |
| 4,054,881 | A | 10/1977 | Raab |
| 4,058,114 | A | 11/1977 | Soldner |
| 4,117,337 | A | 9/1978 | Staats |
| 4,173,228 | A | 11/1979 | Van Steenwyk et al. |
| 4,182,312 | A | 1/1980 | Mushabac |
| 4,202,349 | A | 5/1980 | Jones |
| 4,209,254 | A | 6/1980 | Reymond et al. |
| 4,228,799 | A | 10/1980 | Anichkov et al. |
| 4,256,112 | A | 3/1981 | Kopf et al. |
| 4,259,725 | A | 3/1981 | Andrews et al. |
| 4,262,306 | A | 4/1981 | Renner |
| 4,287,809 | A | 9/1981 | Egli et al. |
| 4,298,874 | A | 11/1981 | Kuipers |
| 4,314,251 | A | 2/1982 | Raab |
| 4,317,078 | A | 2/1982 | Weed et al. |
| 4,319,136 | A | 3/1982 | Jinkins |
| 4,328,548 | A | 5/1982 | Crow et al. |
| 4,328,813 | A | 5/1982 | Ray |
| 4,339,953 | A | 7/1982 | Iwasaki |
| 4,341,220 | A | 7/1982 | Perry |
| 4,346,384 | A | 8/1982 | Raab |
| 4,358,856 | A | 11/1982 | Stivender et al. |
| 4,368,536 | A | 1/1983 | Pfeiler |
| 4,396,885 | A | 8/1983 | Constant |
| 4,396,945 | A | 8/1983 | DiMatteo et al. |
| 4,398,540 | A | 8/1983 | Takemura et al. |
| 4,403,321 | A | 9/1983 | Kruger |
| 4,418,422 | A | 11/1983 | Richter et al. |
| 4,419,012 | A | 12/1983 | Stephenson et al. |
| 4,422,041 | A | 12/1983 | Lienau |
| 4,431,005 | A | 2/1984 | McCormick |
| 4,457,311 | A | 7/1984 | Sorenson et al. |
| 4,485,815 | A | 12/1984 | Amplatz |
| 4,506,676 | A | 3/1985 | Duska |
| 4,543,959 | A | 10/1985 | Sepponen |
| 4,548,208 | A | 10/1985 | Niemi |
| 4,571,834 | A | 2/1986 | Fraser et al. |
| 4,572,198 | A | 2/1986 | Codrington |
| 4,583,538 | A | 4/1986 | Onik et al. |
| 4,584,577 | A | 4/1986 | Temple |
| 4,592,352 | A | 6/1986 | Patil |
| 4,602,622 | A | 7/1986 | Bar et al. |
| 4,608,977 | A | 9/1986 | Brown |
| 4,613,866 | A | 9/1986 | Blood |
| 4,617,925 | A | 10/1986 | Laitinen |
| 4,618,978 | A | 10/1986 | Cosman |
| 4,621,628 | A | 11/1986 | Brudermann |
| 4,625,718 | A | 12/1986 | Olerud et al. |
| 4,638,798 | A | 1/1987 | Shelden et al. |
| 4,642,786 | A | 2/1987 | Hansen |
| 4,645,343 | A | 2/1987 | Stockdale et al. |
| 4,649,504 | A | 3/1987 | Krouglicof et al. |
| 4,651,732 | A | 3/1987 | Frederick |
| 4,653,509 | A | 3/1987 | Oloff et al. |
| 4,659,971 | A | 4/1987 | Suzuki et al. |
| 4,660,970 | A | 4/1987 | Ferrano |
| 4,673,352 | A | 6/1987 | Hansen |
| 4,686,997 | A | 8/1987 | Oloff et al. |
| 4,688,037 | A | 8/1987 | Krieg |
| 4,701,049 | A | 10/1987 | Beckmann et al. |
| 4,705,395 | A | 11/1987 | Hageniers |
| 4,705,401 | A | 11/1987 | Addleman et al. |
| 4,706,665 | A | 11/1987 | Gouda |
| 4,709,156 | A | 11/1987 | Murphy et al. |
| 4,710,708 | A | 12/1987 | Rorden et al. |
| 4,719,419 | A | 1/1988 | Dawley |
| 4,722,056 | A | 1/1988 | Roberts et al. |
| 4,722,336 | A | 2/1988 | Kim et al. |
| 4,723,544 | A | 2/1988 | Moore et al. |
| 4,727,565 | A | 2/1988 | Ericson |
| RE32,619 | E | 3/1988 | Damadian |
| 4,733,661 | A | 3/1988 | Palestrant |
| 4,733,969 | A | 3/1988 | Case et al. |
| 4,737,032 | A | 4/1988 | Addleman et al. |
| 4,737,794 | A | 4/1988 | Jones |
| 4,737,921 | A | 4/1988 | Goldwasser et al. |
| 4,742,356 | A | 5/1988 | Kuipers |
| 4,742,815 | A | 5/1988 | Ninan et al. |
| 4,743,770 | A | 5/1988 | Lee |
| 4,743,771 | A | 5/1988 | Sacks et al. |
| 4,745,290 | A | 5/1988 | Frankel et al. |
| 4,750,487 | A | 6/1988 | Zanetti |
| 4,753,528 | A | 6/1988 | Hines et al. |
| 4,760,851 | A | 8/1988 | Fraser et al. |
| 4,761,072 | A | 8/1988 | Pryor |
| 4,764,016 | A | 8/1988 | Johansson |
| 4,771,787 | A | 9/1988 | Wurster et al. |
| 4,779,212 | A | 10/1988 | Levy |
| 4,782,239 | A | 11/1988 | Hirose et al. |
| 4,788,481 | A | 11/1988 | Niwa |
| 4,791,934 | A | 12/1988 | Brunnett |
| 4,793,355 | A | 12/1988 | Crum et al. |
| 4,794,262 | A | 12/1988 | Sato et al. |
| 4,797,907 | A | 1/1989 | Anderton |
| 4,803,976 | A | 2/1989 | Frigg et al. |
| 4,804,261 | A | 2/1989 | Kirschen |
| 4,805,615 | A | 2/1989 | Carol |
| 4,809,694 | A | 3/1989 | Ferrara |
| 4,821,200 | A | 4/1989 | Oberg |
| 4,821,206 | A | 4/1989 | Arora |
| 4,821,731 | A | 4/1989 | Martinelli et al. |
| 4,822,163 | A | 4/1989 | Schmidt |
| 4,825,091 | A | 4/1989 | Breyer et al. |
| 4,829,373 | A | 5/1989 | Leberl et al. |
| 4,836,778 | A | 6/1989 | Baumrind et al. |
| 4,838,265 | A | 6/1989 | Cosman et al. |
| 4,841,967 | A | 6/1989 | Chang et al. |
| 4,845,771 | A | 7/1989 | Wislocki et al. |
| 4,849,692 | A | 7/1989 | Blood |
| 4,860,331 | A | 8/1989 | Williams et al. |
| 4,862,893 | A | 9/1989 | Martinelli |
| 4,869,247 | A | 9/1989 | Howard, III et al. |
| 4,875,165 | A | 10/1989 | Fencil et al. |
| 4,875,478 | A | 10/1989 | Chen |
| 4,884,566 | A | 12/1989 | Mountz et al. |
| 4,889,526 | A | 12/1989 | Rauscher et al. |
| 4,896,673 | A | 1/1990 | Rose et al. |
| 4,905,698 | A | 3/1990 | Strohl, Jr. et al. |
| 4,923,459 | A | 5/1990 | Nambu |
| 4,931,056 | A | 6/1990 | Ghajar et al. |
| 4,943,296 | A | 7/1990 | Funakubo et al. |
| 4,945,305 | A | 7/1990 | Blood |
| 4,945,914 | A | 8/1990 | Allen |
| 4,951,653 | A | 8/1990 | Fry et al. |

4,955,891 A 9/1990 Carol
4,961,422 A 10/1990 Marchosky et al.
4,971,069 A 11/1990 Gracovetsky
4,977,655 A 12/1990 Martinelli
4,989,608 A 2/1991 Ratner
4,991,579 A 2/1991 Allen
5,002,058 A 3/1991 Martinelli
5,005,592 A 4/1991 Cartmell
5,013,317 A 5/1991 Cole et al.
5,016,639 A 5/1991 Allen
5,017,139 A 5/1991 Mushabac
5,027,818 A 7/1991 Bova et al.
5,030,196 A 7/1991 Inoue
5,030,222 A 7/1991 Calandruccio et al.
5,031,203 A 7/1991 Trecha
5,042,486 A 8/1991 Pfeiler et al.
5,047,036 A 9/1991 Koutrouvelis
5,050,608 A 9/1991 Watanabe et al.
5,054,492 A 10/1991 Scribner et al.
5,057,095 A 10/1991 Fabian
5,059,789 A 10/1991 Salcudean
5,078,140 A 1/1992 Kwoh
5,079,699 A 1/1992 Tuy et al.
5,080,662 A 1/1992 Paul
5,086,401 A 2/1992 Glassman et al.
5,094,241 A 3/1992 Allen
5,097,839 A 3/1992 Allen
5,098,426 A 3/1992 Sklar et al.
5,099,845 A 3/1992 Besz et al.
5,099,846 A 3/1992 Hardy
5,105,829 A 4/1992 Fabian et al.
5,107,839 A 4/1992 Houdek et al.
5,107,843 A 4/1992 Aarnio et al.
5,107,862 A 4/1992 Fabian et al.
5,109,194 A 4/1992 Cantaloube
5,119,817 A 6/1992 Allen
5,142,930 A 9/1992 Allen et al.
5,143,076 A 9/1992 Hardy et al.
5,152,288 A 10/1992 Hoenig et al.
5,160,337 A 11/1992 Cosman
5,161,536 A 11/1992 Vilkomerson et al.
5,178,164 A 1/1993 Allen
5,178,621 A 1/1993 Cook et al.
5,186,174 A 2/1993 Schlondorff et al.
5,187,475 A 2/1993 Wagener et al.
5,188,126 A 2/1993 Fabian et al.
5,190,059 A 3/1993 Fabian et al.
5,193,106 A 3/1993 DeSena
5,197,476 A 3/1993 Nowacki et al.
5,197,965 A 3/1993 Cherry et al.
5,198,768 A 3/1993 Keren
5,198,877 A 3/1993 Schulz
5,207,688 A 5/1993 Carol
5,211,164 A 5/1993 Allen
5,211,165 A 5/1993 Dumoulin et al.
5,211,176 A 5/1993 Ishiguro et al.
5,212,720 A 5/1993 Landi et al.
5,214,615 A 5/1993 Bauer
5,219,351 A 6/1993 Teubner et al.
5,222,499 A 6/1993 Allen et al.
5,224,049 A 6/1993 Mushabac
5,228,442 A 7/1993 Imran
5,230,338 A 7/1993 Allen et al.
5,230,623 A 7/1993 Guthrie et al.
5,233,990 A 8/1993 Barnea
5,237,996 A 8/1993 Waldman et al.
5,249,581 A 10/1993 Horbal et al.
5,251,127 A 10/1993 Raab
5,251,635 A 10/1993 Dumoulin et al.
5,253,647 A 10/1993 Takahashi et al.
5,255,680 A 10/1993 Darrow et al.
5,257,636 A 11/1993 White
5,257,998 A 11/1993 Ota et al.
5,261,404 A 11/1993 Mick et al.
5,265,610 A 11/1993 Darrow et al.
5,265,611 A 11/1993 Hoenig et al.
5,269,759 A 12/1993 Hernandez et al.
5,271,400 A 12/1993 Dumoulin et al.
5,273,025 A 12/1993 Sakiyama et al.
5,274,551 A 12/1993 Corby, Jr.
5,279,309 A 1/1994 Taylor et al.
5,285,787 A 2/1994 Machida
5,291,199 A 3/1994 Overman et al.
5,291,889 A 3/1994 Kenet et al.
5,295,200 A 3/1994 Boyer
5,295,483 A 3/1994 Nowacki et al.
5,297,549 A 3/1994 Beatty et al.
5,299,253 A 3/1994 Wessels
5,299,254 A 3/1994 Dancer et al.
5,299,288 A 3/1994 Glassman et al.
5,300,080 A 4/1994 Clayman et al.
5,305,091 A 4/1994 Gelbart et al.
5,305,203 A 4/1994 Raab
5,306,271 A 4/1994 Zinreich et al.
5,307,072 A 4/1994 Jones, Jr.
5,309,913 A 5/1994 Kormos et al.
5,315,630 A 5/1994 Sturm et al.
5,316,024 A 5/1994 Hirschi et al.
5,318,025 A 6/1994 Dumoulin et al.
5,320,111 A 6/1994 Livingston
5,325,728 A 7/1994 Zimmerman et al.
5,325,873 A 7/1994 Hirschi et al.
5,329,944 A 7/1994 Fabian et al.
5,330,485 A 7/1994 Clayman et al.
5,333,168 A 7/1994 Fernandes et al.
5,353,795 A 10/1994 Souza et al.
5,353,800 A 10/1994 Pohndorf et al.
5,353,807 A 10/1994 DeMarco
5,359,417 A 10/1994 Müller et al.
5,368,030 A 11/1994 Zinreich et al.
5,371,778 A 12/1994 Yanof et al.
5,375,596 A 12/1994 Twiss et al.
5,377,678 A 1/1995 Dumoulin et al.
5,383,454 A 1/1995 Bucholz
5,385,146 A 1/1995 Goldreyer
5,385,148 A 1/1995 Lesh et al.
5,386,828 A 2/1995 Owens et al.
5,389,101 A 2/1995 Heilbrun et al.
5,391,199 A 2/1995 Ben-Haim
5,394,457 A 2/1995 Leibinger et al.
5,394,875 A 3/1995 Lewis et al.
5,397,329 A 3/1995 Allen
5,398,684 A 3/1995 Hardy
5,399,146 A 3/1995 Nowacki et al.
5,400,384 A 3/1995 Fernandes et al.
5,402,801 A 4/1995 Taylor
5,408,409 A 4/1995 Glassman et al.
5,413,573 A 5/1995 Koivukangas
5,417,210 A 5/1995 Funda et al.
5,419,325 A 5/1995 Dumoulin et al.
5,423,334 A 6/1995 Jordan
5,425,367 A 6/1995 Shapiro et al.
5,425,382 A 6/1995 Golden et al.
5,426,683 A 6/1995 O'Farrell, Jr. et al.
5,426,687 A 6/1995 Goodall et al.
5,427,097 A 6/1995 Depp
5,429,132 A 7/1995 Guy et al.
5,433,198 A 7/1995 Desai
RE35,025 E 8/1995 Anderton
5,437,277 A 8/1995 Dumoulin et al.
5,443,066 A 8/1995 Dumoulin et al.
5,443,489 A 8/1995 Ben-Haim 5,444,756 A 8/1995 Pai et al.
5,445,144 A 8/1995 Wodicka et al.
5,445,150 A 8/1995 Dumoulin et al.
5,445,166 A 8/1995 Taylor
5,446,548 A 8/1995 Gerig et al.
5,447,154 A 9/1995 Cinquin et al.
5,448,610 A 9/1995 Yamamoto et al.
5,453,686 A 9/1995 Anderson
5,456,718 A 10/1995 Szymaitis
5,457,641 A 10/1995 Zimmer et al.
5,458,718 A 10/1995 Venkitachalam
5,464,446 A 11/1995 Dreessen et al.
5,469,847 A 11/1995 Zinreich et al.
5,478,341 A 12/1995 Cook et al.
5,478,343 A 12/1995 Ritter
5,480,422 A 1/1996 Ben-Haim
5,480,439 A 1/1996 Bisek et al.
5,483,961 A 1/1996 Kelly et al.
5,484,437 A 1/1996 Michelson
5,485,849 A 1/1996 Panescu et al.
5,487,391 A 1/1996 Panescu
5,487,729 A 1/1996 Avellanet et al.
5,487,757 A 1/1996 Truckai et al.
5,490,196 A 2/1996 Rudich et al.
5,494,034 A 2/1996 Schlondorff et al.
5,503,416 A 4/1996 Aoki et al.
5,513,637 A 5/1996 Twiss et al.
5,514,146 A 5/1996 Lam et al.
5,515,160 A 5/1996 Schulz et al.
5,517,990 A 5/1996 Kalfas et al.
5,520,660 A 5/1996 Loos et al.
5,526,576 A 6/1996 Fuchs et al.
5,531,227 A 7/1996 Schneider
5,531,520 A 7/1996 Grimson et al.
5,542,938 A 8/1996 Avellanet et al.
5,543,951 A 8/1996 Moehrmann
5,546,940 A 8/1996 Panescu et al.
5,546,949 A 8/1996 Frazin et al.
5,546,951 A 8/1996 Ben-Haim
5,551,429 A 9/1996 Fitzpatrick et al.
5,558,091 A 9/1996 Acker et al.
5,566,681 A 10/1996 Manwaring et al.
5,568,384 A 10/1996 Robb et al.
5,568,809 A 10/1996 Ben-haim
5,571,109 A 11/1996 Bertagnoli
5,572,999 A 11/1996 Funda et al.
5,573,533 A 11/1996 Strul
5,575,794 A 11/1996 Walus et al.
5,575,798 A 11/1996 Koutrouvelis
5,583,909 A 12/1996 Hanover
5,588,430 A 12/1996 Bova et al.
5,590,215 A 12/1996 Allen
5,592,939 A 1/1997 Martinelli
5,595,193 A 1/1997 Walus et al.
5,596,228 A 1/1997 Anderton et al.
5,600,330 A 2/1997 Blood
5,603,318 A 2/1997 Heilbrun et al.
5,603,328 A 2/1997 Zucker et al.
5,611,025 A 3/1997 Lorensen et al.
5,617,462 A 4/1997 Spratt
5,617,857 A 4/1997 Chader et al.
5,619,261 A 4/1997 Anderton
5,622,169 A 4/1997 Golden et al.
5,622,170 A 4/1997 Schulz
5,627,873 A 5/1997 Hanover et al.
5,628,315 A 5/1997 Vilsmeier et al.
5,630,431 A 5/1997 Taylor
5,636,644 A 6/1997 Hart et al.
5,638,819 A 6/1997 Manwaring et al.
5,640,170 A 6/1997 Anderson
5,642,395 A 6/1997 Anderton et al.
5,643,268 A 7/1997 Vilsmeier et al.
5,645,065 A 7/1997 Shapiro et al.
5,646,524 A 7/1997 Gilboa
5,647,361 A 7/1997 Damadian
5,662,111 A 9/1997 Cosman
5,664,001 A 9/1997 Tachibana et al.
5,674,296 A 10/1997 Bryan et al.
5,676,673 A 10/1997 Ferre et al.
5,681,260 A 10/1997 Ueda et al.
5,682,886 A 11/1997 Delp et al.
5,682,890 A 11/1997 Kormos et al.
5,690,108 A 11/1997 Chakeres
5,694,945 A 12/1997 Ben-Haim
5,695,500 A 12/1997 Taylor et al.
5,695,501 A 12/1997 Carol et al.
5,697,377 A 12/1997 Wittkampf
5,702,406 A 12/1997 Vilsmeier et al.
5,711,299 A 1/1998 Manwaring et al.
5,713,946 A 2/1998 Ben-Haim
5,715,822 A 2/1998 Watkins
5,715,836 A 2/1998 Kliegis et al.
5,718,241 A 2/1998 Ben-Haim et al.
5,727,552 A 3/1998 Ryan
5,727,553 A 3/1998 Saad
5,729,129 A 3/1998 Acker
5,730,129 A 3/1998 Darrow et al.
5,730,130 A 3/1998 Fitzpatrick et al.
5,732,703 A 3/1998 Kalfas et al.
5,735,278 A 4/1998 Hoult et al.
5,738,096 A 4/1998 Ben-Haim
5,740,802 A 4/1998 Nafis et al.
5,741,214 A 4/1998 Ouchi et al.
5,742,394 A 4/1998 Hansen
5,744,953 A 4/1998 Hansen
5,748,767 A 5/1998 Raab
5,749,362 A 5/1998 Funda et al.
5,749,835 A 5/1998 Glantz
5,752,513 A 5/1998 Acker et al.
5,755,725 A 5/1998 Druais
RE35,816 E 6/1998 Schulz
5,758,667 A 6/1998 Slettenmark
5,762,064 A 6/1998 Polvani
5,767,669 A 6/1998 Hansen et al.
5,767,960 A 6/1998 Orman
5,769,789 A 6/1998 Wang et al.
5,769,843 A 6/1998 Abela et al.
5,769,861 A 6/1998 Vilsmeier
5,772,594 A 6/1998 Barrick
5,772,661 A 6/1998 Michelson
5,775,322 A 7/1998 Silverstein et al.
5,776,064 A * 7/1998 Kalfas et al. ..... 600/414
5,782,765 A 7/1998 Jonkman
5,787,886 A 8/1998 Kelly et al.
5,792,055 A 8/1998 McKinnon
5,792,147 A 8/1998 Evans et al.
5,795,294 A 8/1998 Luber et al.
5,797,849 A 8/1998 Vesely et al.
5,799,055 A 8/1998 Peshkin et al.
5,799,099 A 8/1998 Wang et al.
5,800,352 A 9/1998 Ferre et al.
5,800,535 A 9/1998 Howard, III
5,802,719 A 9/1998 O'Farrell, Jr. et al.
5,803,089 A 9/1998 Ferre et al.
5,807,252 A 9/1998 Hassfeld et al.
5,810,008 A 9/1998 Dekel et al.
5,810,728 A 9/1998 Kuhn
5,810,735 A 9/1998 Halperin et al.
5,820,553 A 10/1998 Hughes
5,823,192 A 10/1998 Kalend et al.
5,823,958 A 10/1998 Truppe
5,828,725 A 10/1998 Levinson

| | | | |
|---|---|---|---|
| 5,828,770 | A | 10/1998 | Leis et al. |
| 5,829,444 | A | 11/1998 | Ferre et al. |
| 5,831,260 | A | 11/1998 | Hansen |
| 5,833,608 | A | 11/1998 | Acker |
| 5,834,759 | A | 11/1998 | Glossop |
| 5,836,954 | A | 11/1998 | Heilbrun et al. |
| 5,840,024 | A | 11/1998 | Taniguchi et al. |
| 5,840,025 | A | 11/1998 | Ben-Haim |
| 5,843,076 | A | 12/1998 | Webster, Jr. et al. |
| 5,848,967 | A | 12/1998 | Cosman |
| 5,851,183 | A | 12/1998 | Bucholz |
| 5,865,846 | A | 2/1999 | Bryan et al. |
| 5,868,674 | A | 2/1999 | Glowinski et al. |
| 5,868,675 | A | 2/1999 | Henrion et al. |
| 5,871,445 | A | 2/1999 | Bucholz |
| 5,871,455 | A | 2/1999 | Ueno |
| 5,871,487 | A | 2/1999 | Warner et al. |
| 5,873,822 | A | 2/1999 | Ferre et al. |
| 5,882,304 | A | 3/1999 | Ehnholm et al. |
| 5,884,410 | A | 3/1999 | Prinz |
| 5,889,834 | A | 3/1999 | Vilsmeier et al. |
| 5,891,034 | A | 4/1999 | Bucholz |
| 5,891,157 | A | 4/1999 | Day et al. |
| 5,904,691 | A | 5/1999 | Barnett et al. |
| 5,907,395 | A | 5/1999 | Schulz et al. |
| 5,913,820 | A | 6/1999 | Bladen et al. |
| 5,920,395 | A | 7/1999 | Schulz |
| 5,921,992 | A | 7/1999 | Costales et al. |
| 5,923,727 | A | 7/1999 | Navab |
| 5,928,248 | A | 7/1999 | Acker |
| 5,938,603 | A | 8/1999 | Ponzi |
| 5,938,694 | A | 8/1999 | Jaraczewski et al. |
| 5,947,980 | A | 9/1999 | Jensen et al. |
| 5,947,981 | A | 9/1999 | Cosman |
| 5,950,629 | A | 9/1999 | Taylor et al. |
| 5,951,475 | A | 9/1999 | Gueziec et al. |
| 5,951,571 | A | 9/1999 | Audette |
| 5,954,647 | A | 9/1999 | Bova et al. |
| 5,957,844 | A | 9/1999 | Dekel et al. |
| 5,964,796 | A | 10/1999 | Imran |
| 5,967,980 | A | 10/1999 | Ferre et al. |
| 5,967,982 | A | 10/1999 | Barnett |
| 5,968,047 | A | 10/1999 | Reed |
| 5,971,997 | A | 10/1999 | Guthrie et al. |
| 5,976,156 | A | 11/1999 | Taylor et al. |
| 5,980,535 | A | 11/1999 | Barnett et al. |
| 5,983,126 | A | 11/1999 | Wittkampf |
| 5,987,349 | A | 11/1999 | Schulz |
| 5,987,960 | A | 11/1999 | Messner et al. |
| 5,999,837 | A | 12/1999 | Messner et al. |
| 5,999,840 | A | 12/1999 | Grimson et al. |
| 6,001,130 | A | 12/1999 | Bryan et al. |
| 6,006,126 | A | 12/1999 | Cosman |
| 6,006,127 | A | 12/1999 | Van Der Brug et al. |
| 6,013,087 | A | 1/2000 | Adams et al. |
| 6,014,580 | A | 1/2000 | Blume et al. |
| 6,016,439 | A | 1/2000 | Acker |
| 6,019,725 | A | 2/2000 | Vesely et al. |
| 6,024,695 | A | 2/2000 | Taylor et al. |
| 6,050,724 | A | 4/2000 | Schmitz et al. |
| 6,059,718 | A | 5/2000 | Taniguchi et al. |
| 6,063,022 | A | 5/2000 | Ben-Haim |
| 6,071,288 | A | 6/2000 | Carol et al. |
| 6,073,043 | A | 6/2000 | Schneider |
| 6,076,008 | A | 6/2000 | Bucholz |
| 6,096,050 | A | 8/2000 | Audette |
| 6,104,944 | A | 8/2000 | Martinelli |
| 6,118,845 | A | 9/2000 | Simon et al. |
| 6,122,538 | A | 9/2000 | Sliwa, Jr. et al. |
| 6,122,541 | A | 9/2000 | Cosman et al. |
| 6,131,396 | A | 10/2000 | Duerr et al. |
| 6,139,183 | A | 10/2000 | Graumann |
| 6,147,480 | A | 11/2000 | Osadchy et al. |
| 6,149,592 | A | 11/2000 | Yanof et al. |
| 6,156,067 | A | 12/2000 | Bryan et al. |
| 6,161,032 | A | 12/2000 | Acker |
| 6,165,181 | A | 12/2000 | Heilbrun et al. |
| 6,167,296 | A | 12/2000 | Shahidi |
| 6,172,499 | B1 | 1/2001 | Ashe |
| 6,174,330 | B1 | 1/2001 | Stinson |
| 6,175,756 | B1 | 1/2001 | Ferre et al. |
| 6,178,345 | B1 | 1/2001 | Vilsmeier et al. |
| 6,194,639 | B1 | 2/2001 | Botella et al. |
| 6,201,387 | B1 | 3/2001 | Govari |
| 6,203,497 | B1 | 3/2001 | Dekel et al. |
| 6,211,666 | B1 | 4/2001 | Acker |
| 6,223,067 | B1 | 4/2001 | Vilsmeier |
| 6,233,476 | B1 | 5/2001 | Strommer et al. |
| 6,236,875 | B1 | 5/2001 | Bucholz et al. |
| 6,246,231 | B1 | 6/2001 | Ashe |
| 6,259,942 | B1 | 7/2001 | Westermann et al. |
| 6,273,896 | B1 | 8/2001 | Franck et al. |
| 6,285,902 | B1 | 9/2001 | Kienzle, III et al. |
| 6,298,262 | B1 | 10/2001 | Franck et al. |
| 6,314,310 | B1 | 11/2001 | Ben-Haim et al. |
| 6,332,089 | B1 | 12/2001 | Acker et al. |
| 6,341,231 | B1 | 1/2002 | Ferre et al. |
| 6,348,058 | B1 | 2/2002 | Melkent et al. |
| 6,351,659 | B1 | 2/2002 | Vilsmeier |
| 6,381,485 | B1 | 4/2002 | Hunter et al. |
| 6,424,856 | B1 | 7/2002 | Vilsmeier et al. |
| 6,427,314 | B1 | 8/2002 | Acker |
| 6,428,547 | B1 | 8/2002 | Vilsmeier et al. |
| 6,434,415 | B1 | 8/2002 | Foley et al. |
| 6,437,567 | B1 | 8/2002 | Schenck et al. |
| 6,445,943 | B1 | 9/2002 | Ferre et al. |
| 6,470,207 | B1 | 10/2002 | Simon et al. |
| 6,474,341 | B1 | 11/2002 | Hunter et al. |
| 6,478,802 | B2 | 11/2002 | Kienzle, III et al. |
| 6,484,049 | B1 | 11/2002 | Seeley et al. |
| 6,490,475 | B1 | 12/2002 | Seeley et al. |
| 6,493,573 | B1 | 12/2002 | Martinelli et al. |
| 6,498,944 | B1 | 12/2002 | Ben-Haim et al. |
| 6,499,488 | B1 | 12/2002 | Hunter et al. |
| 6,516,046 | B1 | 2/2003 | Fröhlich et al. |
| 6,527,443 | B1 | 3/2003 | Vilsmeier et al. |
| 6,551,325 | B2 | 4/2003 | Neubauer et al. |
| 6,584,174 | B2 | 6/2003 | Schubert et al. |
| 6,609,022 | B2 | 8/2003 | Vilsmeier et al. |
| 6,611,700 | B1 | 8/2003 | Vilsmeier et al. |
| 6,640,128 | B2 | 10/2003 | Vilsmeier et al. |
| 6,694,162 | B2 | 2/2004 | Hartlep |
| 6,701,179 | B1 | 3/2004 | Martinelli et al. |
| 2001/0007918 | A1 | 7/2001 | Vilsmeier et al. |
| 2002/0095081 | A1 | 7/2002 | Vilsmeier |
| 2004/0024309 | A1 | 2/2004 | Ferre et al. |

FOREIGN PATENT DOCUMENTS

| | | | |
|---|---|---|---|
| DE | 3042343 | A1 | 6/1982 |
| DE | 35 08730 | | 3/1985 |
| DE | 37 17 871 | | 5/1987 |
| DE | 38 38011 | | 11/1988 |
| DE | 3831278 | A1 | 3/1989 |
| DE | 42 13 426 | | 4/1992 |
| DE | 42 25 112 | | 7/1992 |
| DE | 4233978 | C1 | 4/1994 |
| DE | 197 15 202 | | 4/1997 |
| DE | 197 15 202 | A1 * | 4/1997 |
| DE | 197 47 427 | | 10/1997 |
| DE | 197 51 761 | | 11/1997 |
| DE | 198 32 296 | | 7/1998 |
| DE | 10085137 | | 11/2002 |

| | | | | |
|---|---|---|---|---|
| EP | 0018166 | A1 | | 4/1980 |
| EP | 0 018 166 | A1 | * | 4/1980 |
| EP | 0 062 941 | | | 3/1982 |
| EP | 0 119 660 | | | 9/1984 |
| EP | 0 155 857 | | | 1/1985 |
| EP | 0319844 | A1 | | 1/1988 |
| EP | 0 359 733 | B1 | * | 5/1988 |
| EP | 0359773 | B1 | | 5/1988 |
| EP | 0 326 768 | | | 12/1988 |
| EP | 0 326 768 | A2 | * | 12/1988 |
| EP | 0419729 | A1 | | 9/1989 |
| EP | 0350996 | A1 | | 1/1990 |
| EP | 0651968 | A1 | | 8/1990 |
| EP | 0 427 358 | | | 10/1990 |
| EP | 0 427 358 | A1 | * | 10/1990 |
| EP | 0 501 993 | B1 | * | 11/1990 |
| EP | 0501993 | B1 | | 11/1990 |
| EP | 0 456 103 | | | 5/1991 |
| EP | 0 456 103 | A2 | * | 7/1991 |
| EP | 0 469 966 | A1 | * | 7/1991 |
| EP | 0581704 | B1 | | 7/1993 |
| EP | 0655138 | B1 | | 8/1993 |
| EP | 0894473 | A2 | | 1/1995 |
| EP | 0469966 | | | 8/1995 |
| EP | 0 908 146 | | | 10/1998 |
| EP | 0 930 046 | | | 10/1998 |
| FR | 2417970 | | | 2/1979 |
| FR | 2 618 211 | | | 7/1987 |
| GB | 2 094 590 | | | 2/1982 |
| GB | 2 164 856 | | | 10/1984 |
| JP | 61-94639 | | | 10/1984 |
| JP | 62-327 | | | 6/1985 |
| JP | 63-240851 | | | 3/1987 |
| JP | 3-267054 | | | 3/1990 |
| JP | 2765738 | | | 6/1998 |
| WO | WO 88/09151 | | | 12/1988 |
| WO | WO 89/05123 | | | 6/1989 |
| WO | WO 90/05494 | | | 11/1989 |
| WO | WO 91/03982 | | | 4/1991 |
| WO | WO 91/04711 | | | 4/1991 |
| WO | WO 91/07726 | | | 5/1991 |
| WO | WO 92/03090 | | | 3/1992 |
| WO | WO 92/06645 | | | 4/1992 |
| WO | WO 94/04938 | | | 3/1994 |
| WO | WO 95/07055 | | | 9/1994 |
| WO | WO 94/23647 | | | 10/1994 |
| WO | WO 94/24933 | | | 11/1994 |
| WO | WO 96/11624 | | * | 4/1995 |
| WO | WO 96/32059 | | | 11/1995 |
| WO | WO 96/11624 | | | 4/1996 |
| WO | WO 96/32059 | | * | 10/1996 |
| WO | WO 97/49453 | | | 6/1997 |
| WO | WO 97/36192 | | | 10/1997 |
| WO | WO 97/40764 | | | 11/1997 |
| WO | WO 99/23956 | | | 11/1997 |
| WO | WO 98/08554 | | | 3/1998 |
| WO | WO 98/38908 | | | 9/1998 |
| WO | WO 99/15097 | | | 9/1998 |
| WO | WO 99/21498 | | | 10/1998 |
| WO | WO 99/27839 | | | 12/1998 |
| WO | WO 99/33406 | | | 12/1998 |
| WO | WO 99/38449 | | | 1/1999 |
| WO | WO 99/52094 | | | 4/1999 |
| WO | WO 99/26549 | | | 6/1999 |
| WO | WO 99/29253 | | | 6/1999 |
| WO | WO 99/37208 | | | 7/1999 |
| WO | WO 99/60939 | | | 12/1999 |
| WO | WO 01/30437 | A1 | | 5/2001 |

OTHER PUBLICATIONS

Office Action mailed Sep. 21, 2008 in pending U.S. Appl. No. 11/451,594, filed Jun. 12, 2006.

Adams et al., Computer–Assisted Surgery, IEEE Computer Graphics & Applications, pp. 43–51, (May 1990).

Adams et al., "Orientation Aid for Head and Neck Surgeons," Innov. Tech. Biol. Med., vol. 13, No. 4, 1992, pp. 409–424.

Barrick et al., "Prophylactic Intramedullary Fixation of the Tibia for Stress Fracture in a Professional Athlete," Journal of Orthopaedic Trauma, vol. 6, No. 2, pp. 241–244 (1992).

Barrick et al., "Technical Difficulties with the Brooker–Wills Nail in Acute Fractures of the Femur," Journal of Orthopaedic Trauma, vol. 4, No. 2, pp. 144–150 (1990).

Barrick, "Distal Locking Screw Insertion Using a Cannulated Drill Bit: Technical Note," Journal of Orthopaedic Trauma, vol. 7, No. 3, 1993, pp. 248–251.

Batnitzky et al., "Three–Dimensinal Computer Reconstructions of Brain Lesions from Surface Contours Provided by Computed Tomography: A Prospectus," Neurosurgery, vol. 11, No. 1, Part 1, 1982, pp. 73–84.

Benzel et al., "Magnetic Source Imaging: a Review of the Magnes System of Biomagnetic Technologies Incorporated," Neurosurgery, vol. 33, No. 2 (Aug. 1993), pp. 252–259.

Bergstrom et al. Stereotaxic Computed Tomography, Am. J. Roentgenol, vol. 127 pp. 167–170 (1976).

Bouazza–Marouf et al.; "Robotic–Assisted Internal Fixation of Femoral Fractures", IMECHE., pp. 51–58 (1995).

Brack et al., "Accurate X–ray Based Navigation in Computer–Assisted Orthopedic Surgery," CAR '98, pp. 716–722.

Brown, R., M.D., A Stereotactic Head Frame for Use with CT Body Scanners, Investigative Radiology © J.B. Lippincott Company, pp. 300–304 (Jul.–Aug. 1979).

Bryan, "Bryan Cervical Disc System Single Level Surgical Technique", Spinal Dynamics, 2002, pp. 1–33.

Bucholz et al., "Variables affecting the accuracy of stereotactic localizationusing computerized tomography," Journal of Neurosurgery, vol. 79, Nov. 1993, pp. 667–673.

Bucholz, R.D., et al. Image–guided surgical techniques for infections and trauma of the central nervous system, Neurosurg. Clinics of N.A., vol. 7, No. 2, pp. 187–200 (1996).

Bucholz, R.D., et al., A Comparison of Sonic Digitizers Versus Light Emitting Diode–Based Localization, Interactiv Image–Guided Neurosurgery, Chapter 16, pp. 179–200 (1993).

Bucholz, R.D., et al., Intraoperative localization using a three dimensional optical digitizer, SPIE—The Intl. Soc. for Opt. Eng., vol. 1894, pp. 312–322 (Jan. 17–19, 1993).

Bucholz, R.D., et al., Intraoperative Ultrasonic Brain Shift Monitor and Analysis, Stealth Station Marketing Brochure (2 pages) (undated).

Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer–Assisted Surgery, Grenoble, France, pp. 459–466 (Mar. 19–22, 1997).

Champleboux et al., "Accurate Calibration of Cameras and Range Imaging Sensors: the NPBS Method," IEEE International Conference on Robotics and Automation, Nice, France, May 1992.

Champleboux, "Utilisation de Fonctions Splines pour la Mise au Point D'un Capteur Tridimensionnel sans Contact," Quelques Applications Medicales, Jul. 1991.

Cinquin et al., "Computer Assisted Medical Interventions," IEEE Engineering in Medicine and Biology, May/Jun. 1995, pp. 254–263.

Cinquin et al., "Computer Assisted Medical Interventions," International Advanced Robotics Programme, Sep. 1989, pp. 63–65.

Clarysse et al., "A Computer–Assisted System for 3–D Frameless Localization in Stereotaxic MRI," IEEE Transactions on Medical Imaging, vol. 10, No. 4, Dec. 1991, pp. 523–529.

Cutting M.D. et al., Optical Tracking of Bone Fragments During Craniofacial Surgery, Second Annual International Symposium on Medical Robotics and Computer Assisted Surgery, pp. 221–225, (Nov. 1995).

Feldmar et al., "3D–2D Projective Registration of Free–Form Curves and Surfaces," Rapport de recherche (Inria Sophia Antipolis), 1994, pp. 1–44.

Foley et al., "Fundamentals of Interactive Computer Graphics," The Systems Programming Series, Chapter 7, Jul. 1984, pp. 245–266.

Foley et al., "Image–guided Intraoperative Spinal Localization," Intraoperative Neuroprotection, Chapter 19, 1996, pp. 325–340.

Foley, "The StealthStation: Three–Dimensional Image–Interactive Guidance for the Spine Surgeon," Spinal Frontiers, Apr. 1996, pp. 7–9.

Friets, E.M., et al. A Frameless Stereotaxic Operating Microscope for Neurosurgery, IEEE Trans. on Biomed. Eng., vol. 36, No. 6, pp. 608–617 (Jul. 1989).

Gallen, C.C., et al., Intracranial Neurosurgery Guided by Functional Imaging, Surg. Neurol., vol. 42, pp. 523–530 (1994).

Galloway, R.L., et al., Interactive Image–Guided Neurosurgery, IEEE Trans. on Biomed. Eng., vol. 89, No. 12, pp. 1226–1231 (1992).

Galloway, R.L., Jr. et al, Optical localization for interactive, image–guided neurosurgery, SPIE, vol. 2164, pp. 137–145 (undated.

Germano, "Instrumentation, Technique and Technology", Neurosurgery, vol. 37, No. 2, Aug. 1995, pp. 348–350.

Gildenberg et al., "Calculation of Stereotactic Coordinates from the Computed Tomographic Scan," Neurosurgery, vol. 10, No. 5, May 1982, pp. 580–586.

Gomez, C.R., et al., Transcranial Doppler Ultrasound Following Closed Head Injury: Vasospasm or Vasoparalysis?, Surg. Neurol., vol. 35, pp. 30–35 (1991).

Gonzalez, "Digital Image Fundamentals," Digital Image Processing, Second Edition, 1987, pp. 52–54.

Gottesfeld Brown et al., "Registration of Planar Film Radiographs with Computer Tomography," Proceedings of MMBIA, Jun. '96, pp. 42–51.

Grimson, W.E.L., An Automatic Registration Method for Frameless Stereotaxy, Image Guided Surgery, and enhanced Reality Visualization, IEEE, pp. 430–436 (1994).

Grimson, W.E.L., et al., Virtual–reality technology is giving surgeons the equivalent of x–ray vision helping them to remove tumors more effectively, to minimize surgical wounds and to avoid damaging critical tissues, Sci. Amer., vol. 280, No. 6, pp. 62–69 (Jun. 1999).

Gueziec et al., "Registration of Computed Tomography Data to a Surgical Robot Using Fluoroscopy: A Feasibility Study," Computer Science/Mathematics, Sep. 27, 1996, 6 pages.

Guthrie, B.L., Graphic–Interactive Cranial Surgery: The Operating Arm System, Handbook of Stereotaxy Using the CRW Apparatus, Chapter 13, pp. 193–211 (undated.

Hamadeh et al, "Kinematic Study of Lumbar Spine Using Functional Radiographies and 3D/2D Registration," TIMC UMR 5525—IMAG.

Hamadeh et al., "Automated 3–Dimensional Computed Tomographic and Fluorscopic Image Registration," Computer Aided Surgery (1998), 3:11–19.

Hamadeh et al., "Towards Automatic Registration Between CT and X–ray Images: Cooperation Between 3D/2D Registration and 2D Edge Detection," MRCAS '95, pp. 39–46.

Hardy, T., M.D., et al., CASS: A Program for Computer Assist Stereotaxic Surgery, The Fifth Annual Symposium on Computer Applications in Medical Care, Proceedings, Nov. 1–4, 1981, IEEE, pp. 1116–1126, (1981).

Hatch, "Reference–Display System for the Integration of CT Scanning and the Operating Microscope," Thesis, Thayer School of Engineering, Oct. 1984, pp. 1–189.

Hatch, et al., "Reference–Display System for the Integration of CT Scanning and the Operating Microscope", Proceedings of the Eleventh Annual Northeast Bioengineering Conference, Mar. 14–15, 1985, pp. 252–254.

Heilbrun et al., "Preliminary experience with Brown–Roberts–Wells (BRW) computerized tomography stereotaxic guidance system," Journal of Neurosurgery, vol. 59, Aug. 1983, pp. 217–222.

Heilbrun, M.D., Progressive Technology Applications, Neurosurgery for the Third Millenium, Chapter 15, J. Whitaker & Sons, Ltd., Amer. Assoc. of Neurol. Surgeons, pp. 191–198 (1992).

Heilbrun, M.P., Computed Tomography—Guided Stereotactic Systems, Clinical Neurosurgery, Chapter 31, pp. 564–581 (1983).

Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94–98 (1992).

Henderson et al., "An Accurate and Ergonomic Method of Registration for Image–guided Neurosurgery," Computerized Medical Imaging and Graphics, vol. 18, No. 4, Jul.–Aug. 1994, pp. 273–277.

Hoerenz, "The Operating Microscope I. Optical Principles, Illumination Systems, and Support Systems," Journal of Microsurgery, vol. 1, 1980, pp. 364–369.

Hofstetter et al., "Fluoroscopy Based Surgical Navigation—Concept and Clinical Applications," Computer Assisted Radiology and Surgery, 1997, pp. 956–960.

Horner et al., "A Comparison of CT–Stereotaxic Brain Biopsy Techniques," Investigative Radiology, Sep.–Oct. 1984, pp. 367–373.

Hounsfield, "Computerized transverse axial scanning (tomography): Part 1. Description of system," British Journal of Radiology, vol. 46, No. 552, Dec. 1973, pp. 1016–1022.

Jacques et al., "A Computerized Microstereotactic Method to Approach, 3–Dimensionally Reconstruct, Remove and Adjuvantly Treat Small CNS Lesions," Applied Neurophysiology, vol. 43, 1980, pp. 176–182.

Jacques et al., "Computerized three–dimensional stereotaxic removal of small central nervous system lesion in patients," J. Neurosurg., vol. 53, Dec. 1980, pp. 816–820.

Joskowicz et al., "Computer–Aided Image–Guided Bone Fracture Surgery: Concept and Implementation," CAR '98, pp. 710–715.

Kall, B., The Impact of Computer and Imaging Technology on Stereotactic Surgery, Proceedings of the Meeting of the American Society for Stereotactic and Functional Neurosurgery, pp. 10–22 (1987).

Kato, A., et al., A frameless, armless navigational system for computer–assisted neurosurgery, J. Neurosurg., vol. 74, pp. 845–849 (May 1991).

Kelly et al., "Computer–assisted stereotaxic laser resection of intra–axial brain neoplasms," Journal of Neurosurgery, vol. 64, Mar. 1986, pp. 427–439.

Kelly et al., "Precision Resection of Intra–Axial CNS Lesions by CT–Based Stereotactic Craniotomy and Computer Monitored CO2 Laser," Acta Neurochirurgica, vol. 68, 1983, pp. 1–9.

Kelly, P.J., Computer Assisted Stereotactic Biopsy and Volumetric Resection of Pediatric Brain Tumors, Brain Tumors in Children, Neurologic Clinics, vol. 9, No. 2, pp. 317–336 (May 1991).

Kelly, P.J., Computer–Directed Stereotactic Resection of Brain Tumors, Neurologica Operative Atlas, vol. 1, No. 4, pp. 299–313 (1991).

Kelly, P.J., et al., Results of Computed Tomography–based Computer–assisted Stereotactic Resection of Metastatic Intracranial Tumors, Neurosurgery, vol. 22, No. 1, Part 1, 1988, pp. 7–17 (Jan. 1988).

Kelly, P.J., Stereotactic Imaging, Surgical Planning and Computer–Assisted Resection of Intracranial Lesions: Methods and Results, Advances and Technical Standards in Neurosurgery, vol. 17, pp. 78–118, (1990).

Kim, W.S. et al., A Helmet Mounted Display for Telerobotics, IEEE, pp. 543–547 (1988).

Klimek, L., et al., Long–Term Experience with Different Types of Localization Systems in Skull–Base Surgery, Ear, Nose & Throat Surgery, Chapter 51, pp. 635–638 (undated).

Kosugi, Y., et al., An Articulated Neurosurgical Navigation System Using MRI and CT Images, IEEE Trans. on Biomed, Eng. vol. 35, No. 2, pp. 147–152 (Feb. 1988).

Krybus, W., et al., Navigation Support for Surgery by Means of Optical Position Detection, Computer Assisted Radiology Proceed. of the Intl. Symp. CAR '91 Computed Assisted Radiology, pp. 362–366 (Jul. 3–6, 1991).

Kwoh, Y.S., Ph.D., et al., A New Computerized Tomographic–Aided Robotic Stereotaxis System, Robotics Age, vol. 7, No. 6, pp. 17–22 (Jun. 1985).

Laitinen et al., "An Adapter for Computed Tomography–Guided, Stereotaxis," Surg. Neurol., 1985, pp. 559–566.

Laitinen, "Noninvasive multipurpose stereoadapter," Neurological Research, Jun. 1987, pp. 137–141.

Lavallee et al, "Matching 3–D Smooth Surfaces with their 2–D Projections using 3–D Distance Maps," SPIE, vol. 1570, Geometric Methods in Computer Vision, 1991, pp. 322–336.

Lavallee et al., "Computer Assisted Driving of a Needle into the Brain," Proceedings of the International Symposium CAR '89, Computer Assisted Radiology, 1989, pp. 416–420.

Lavallee et al., "Computer Assisted Interventionist Imaging: The Instance of Stereotactic Brain Surgery," North–Holland MEDINFO 89, Part 1, 1989, pp. 613–617.

Lavallee et al., "Computer Assisted Spine Surgery: A Technique For Accurate Transpedicular Screw Fixation Using CT Data and a 3–D Optical Localizer," TIMC, Faculte de Medecine de Grenoble.

Lavallee et al., "Image guided operating robot: a clinical application in stereotactic neurosurgery," Proceedings of the 1992 IEEE Internation Conference on Robotics and Automation, May 1992, pp. 618–624.

Lavallee et al., "Matching of Medical Images for Computed and Robot Assisted Surgery," IEEE EMBS, Orlando, 1991.

Lavallee, "A New System for Computer Assisted Neurosurgery," IEEE Engineering in Medicine & Biology Society 11th Annual International Conference, 1989, pp. 0926–0927.

Lavallee, "VI Adaption de la Methodologie a Quelques Applications Cliniques," Chapitre VI, pp. 133–148.

Lavalle, S., et al., Computer Assisted Knee Anterior Cruciate Ligament Reconstruction First Clinical Tests, Proceedings of the First International Symposium on Medical Robotics and Computer Assisted Surgery, pp. 11–16 (Sep. 1994).

Lavallee, S., et al., Computer Assisted Medical Interventions, NATO ASI Series, vol. F 60, 3d Imaging in Medic., pp. 301–312 (1990).

Leavitt, D.D., et al., Dynamic Field Shaping to Optimize Stereotactic Radiosurgery, I.J. Rad. Onc. Biol. Physc., vol. 21, pp. 1247–1255 (1991).

Leksell et al., "Stereotaxis and Tomography—A Technical Note," ACTA Neurochirurgica, vol. 52, 1980, pp. 1–7.

Lemieux et al., "A Patient–to–Computed–Tomography Image Registration Method Based on Digitally Reconstructed Radiographs," Med. Phys. 21 (11), Nov. 1994, pp. 1749–1760.

Levin et al., "The Brain: Integrated Three–dimensional Display of MR and PET Images," Radiology, vol. 172, No. 3, Sep. 1989, pp. 783–789.

Maurer, Jr., et al., Registration of Head CT Images to Physical Space Using a Weighted Combination of Points and Surfaces, IEEE Trans. on Med. Imaging, vol. 17, No. 5, pp. 753–761 (Oct. 1998).

Mazier et al., "Computer–Assisted Interventionist Imaging: Application to the Vertebral Column Surgery," Annual International Conference of the IEEE Engineering in Medicine and Biology Society, vol. 12, No. 1, 1990, pp. 0430–0431.

Mazier et al., Chirurgie de la Colonne Vertebrale Assistee par Ordinateur: Appication au Vissage Pediculaire, Innov. Tech. Biol. Med., vol. 11, No. 5, 1990, pp. 559–566.

McGirr, S., M.D., et al., Stereotactic Resection of Juvenile Pilocytic Astrocytomas of the Thalamus and Basal Ganglia, Neurosurgery, vol. 20, No. 3, pp. 447–452, (1987).

Merloz, et al., "Computer Assisted Spine Surgery", Clinical Assisted Spine Surgery, No. 337, pp. 86–96.

Ng, W.S. et al., Robotic Surgery—A First–Hand Experience in Transurethral Resection of the Prostate Surgery, IEEE Eng. in Med. and Biology, pp. 120–125 (Mar. 1993).

Pelizzari et al., "Accurate Three–Dimensional Registration of CT, PET, and/or MR Images of the Brain," Journal of Computer Assisted Tomography, Jan./Feb. 1989, pp. 20–26.

Pelizzari et al., "Interactive 3D Patient–Image Registration," Information Processing in Medical Imaging, 12th International Conference, IPMI '91, Jul. 7–12, 136–141 (A.C.F. Colchester et al. eds. 1991).

Pelizzari et al., No. 528—"Three Dimensional Correlation of PET, CT and MRI Images," The Journal of Nuclear Medicine, vol. 28, No. 4, Apr. 1987, p. 682.

Penn, R.D., et al., Stereotactic Surgery with Image Processing of Computerized Tomographic Scans, Neurosurgery, vol. 3, No. 2, pp. 157–163 (Sep.–Oct. 1978).

Phillips et al., "Image Guided Orthopaedic Surgery Design and Analysis," Trans Inst. MC, vol. 17, No. 5, 1995, pp. 251–264.

Pixsys, 3–D Digitizing Accessories, by Pixsys (marketing brochure) (undated) (2 pages).

Potamianos et al., "Intra–Operative Imaging Guidance for Keyhole Surgery Methodology and Calibration," First International Symposium on Medical Robotics and Computer Assisted Surgery, Sep. 22–24, 1994, pp. 98–104.

Prestige Cervical Disc System Surgical Technique, 12 pgs.

Reinhardt et al., "CT–Guided 'Real Time' Stereotaxy," Acta Neurochirurgica, 1989.

Reinhardt, H., et al., A Computer–Assisted Device for Intraoperative CT–Correlated Localization of Brain Tumors, pp. 51–58 (1988).

Reinhardt, H.F. et al., Sonic Stereometry in Microsurgical Procedures for Deep–Seated Brain Tumors and Vascular Malformations, Neurosurgery, vol. 32, No. 1, pp. 51–57 (Jan. 1993).

Reinhardt, H.F., et al., Mikrochirugische Entfernung tiefliegender Gefäβmiβbild ungen mit Hilfe der Sonar–Stereometrie (Microsurgical Removal of Deep–Seated Vascular Malformations Using Sonar Stereometry). Ultraschall in Med. 12, pp. 80–83 (1991).

Reinhardt, Hans. F., Neuronavigation: A Ten–Year Review, Neurosurgery, pp. 329–341 (undated).

Roberts et al., "A frameless stereotaxic integration of computerized tomographic imaging and the operating microscope," J. Neurosurg., vol. 65, Oct. 1986, pp. 545–549.

Rosenbaum et al., "Computerized Tomography Guided Stereotaxis: A New Approach," Applied Neurophysiology, vol. 43, No. 3–5, 1980, pp. 172–173.

Sautot, "Vissage Pediculaire Assiste Par Ordinateur," Sep. 20, 1994.

Schueler et al., "Correction of Image Intensifier Distortion for Three–Dimensional X–Ray Angiography," SPIE Medical Imaging 1995, vol. 2432, pp. 272–279.

Selvik et al., "A Roentgen Stereophotogrammetric System," Acta Radiologica Diagnosis, 1983, pp. 343–352.

Shelden et al., "Development of a computerized microstereotaxic method for localization and removal of minute CNS lesions under direct 3–D vision," J. Neurosurg., vol. 52, 1980, pp. 21–27.

Simon, D.A., Accuracy Validation in Image–Guided Orthopaedic Surgery, Second Annual Intl. Symp. on Med. Rob. an Comp–Assisted surgery, MRCAS '95, pp. 185–192 (undated).

Smith et al., "Computer Methods for Improved Diagnostic Image Display Applied to Stereotactic Neurosurgery," Automedical, vol. 14, 1992, pp. 371–382 (4 unnumbered pages).

Smith et al., "The Neurostation™—A Highly Accurate, Minimally Invasive Solution to Frameless Stereotactic Neurosurgery," Computerized Medical Imaging and Graphics, vol. 18, Jul.–Aug. 1994, pp. 247–256.

Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).

Tan, K., Ph.D., et al., A frameless stereotactic approach to neurosurgical planning based on retrospective patient–image registration, J Neurosurgy, vol. 79, pp. 296–303 (Aug. 1993).

The Laitinen Stereotactic System, E2–E6.

Thompson, et al., A System for Anatomical and Functional Mapping of the Human Thalamus, Computers and Biomedical Research, vol. 10, pp. 9–24 (1977).

Trobraugh, J.W., et al., Frameless Stereotactic Ultrasonography: Method and Applications, Computerized Medical Imaging and Graphics, vol. 18, No. 4, pp. 235–246 (1994).

Viant et al., "A Computer Assisted Orthopaedic System for Distal Locking of Intramedullary Nails," Proc. of MediMEC '95, Bristol, 1995, pp. 86–91.

Von Hanwhr et al., Foreword, Computerized Medical Imagine and Graphics, vol. 18, No. 4, pp. 225–228, (Jul.–Aug. 1994).

Wang, M.Y., et al., An Automatic Technique for Finding and Localizing Externally Attached Markers in CT and MR Volume Images of the Head, IEEE Trans. on Biomed. Eng., vol. 43, No. 6, pp. 627–637 (Jun. 1996).

Watanabe et al., "Three–Dimensional Digitizer (Neuronavigator): New Equipment for Computed Tomography–Guided Stereotaxic Surgery," Surgical Neurology, vol. 27, No. 6, Jun. 1987, pp. 543–547.

Watanabe, "Neuronavigator," Igaku–no–Ayumi, vol. 137, No. 6, May 10, 1986, pp. 1–4.

Watanabe, E., M.D., et al., Open Surgery Assisted by the Neuronavigator, a Stereotactic, Articulated, Sensitive Arm, Neurosurgery, vol. 28, No. 6, pp. 792–800 (1991).

Weese et al., "An Approach to 2D/3D Registration of a Vertebra in 2D X–ray Fluoroscopies with 3D CT Images," pp. 119–128.

Weinstein, et al., Spinal Pedicle Fixation: Reliability and Validity of Roentgenogram–Based Assessment and Surgical Factors on Successful Screw Placement, *Spine,* vol. 13, No. 9, 1988, pp. 1012–1018.*

Kelly, The NeuroStation System for Image–Guided, Frameless Stereotaxy, *Neurosurgery,* vol. 37, No. 2, Aug. 1995, pp. 348–350.*

Vector Vision: The Power of Surgical Tracking, *BrainLab,* 1997.*

J.F. Mallet, et al., Post–Laminectomy Cervical–Thoracic Kyphosis in a Patient with Von Recklinghausen's Disease, *Spinal Frontiers,* vol. Three, Issue One, Apr. 1996, pp. 1–15.*

Bucholz, et al., Image–Guided Surgical Techniques for Infections and Trauma of the Central Nervous System, *Neurosurgery Clinics of North America,* vol. 7, No. 2, Apr. 1996, pp. 187–200.*

Foley, et al., Image–guided Intraoperative Spinal Localization, *Intraoperative Neuroprotection: Monitoring,* Part Three, 1996, pp. 325–340.*

Mazier, et al., Computer Assisted Interventionist Imaging: Application to the Vertebral Column Surgery, *Annual International Conference of the IEEE Engineering in Medicine and Biology Society,* vol. 12, No. 1, 1990, pp. 0430–0431.*

Lavallée, et al., Computer Assisted Medical Interventions, *NATO ASI Series,* vol. F 60, 1990, pp. 301–312.*

Adams et al., Computer–Assisted Surgery, *IEEE Computer Graphics & Applications,* May 1990, pp. 43–51.*

3–D Digitizer Captures the World, *BYTE,* Oct. 1990, p. 43.*

Reinhardt, et al., Interactive Sonar–Operated Device for Stereotactic and Open Surgery, *Proceedings of the Xth Meeting of the World Society for Stereotactic and Functional Neurosurgery,* Maebashi, Japan, Oct. 1989, pp. 393–397.*

Kato, et al., A frameless, armless navigational system for computer–assisted neurosurgery, *J. Neurosurgery* 74 1991, pp. 845–849.*

Smith et al., Multimodality Image Analysis and Display Methods for Improved Tumor Localization in Stereotatic Neurosurgery, *Proceedings of the Annual International Conference of the IEEE Engineering in Medicine and Biology Society,* vol. 13, 1991, p. 0210.*

Sautot et al., Computer Assisted Spine Surgery: a first step toward clinical application in orthopaedics, *IEEE,* 1992, p. 1071–1072.*

Cinquin, et al., GOR: Image Guided Operating Robot. Methodology, Applications, *IEEE EMBS,* Paris 1992, pp. 1–2.*

Alignment Procedure for the PixSys Two–Emitter Offset Probe for the SAC GP–8–3d Sonic Digitizer, *PixSys,* Jul. 2, 1992, pp. 1–4.*

Smith, et al., Computer Methods for Improved Diagnostic Image Display Applied to Stereotactic Neurosurgery, *Automedica,* 1992, vol. 14, pp. 371–382.*

Reinhardt, Neuronavigation: A Ten–Year Review, *Neurosurgery,* 1993, pp. 329–341.*

Bucholz, et al., Intraoperative localization using a three dimensional optical digitizer, *SPIE* vol. 1894, Jan. 17, 1993, pp. 312–322.*

Smith, et al., The Neurostation™ –A Highly Accurate, Minimally Invasive Solution to Frameless Stereotactic Neurosurgery, *Computerized Medical Imaging and Graphics,* vol. 18, 1994, pp. 247–256.*

Bucholz, et al., Halo vest versus spinal fusion for cervical injury: evidence from an outcome study, *J. Neurosurg.,* vol. 70, pp. 884–892.*

Awwad, et al., Post–traumatic Spinal Synovial Cyst with Spondylolysis: CT Features, *Journal of Computer Assisted Tomography,* vol. 13, No. 2, 1989, pp. 334–337.*

* cited by examiner

PERCUTANEOUS REGISTRATION APPARATUS AND METHOD FOR USE IN COMPUTER-ASSISTED SURGICAL NAVIGATION

Matter enclosed in heavy brackets [ ] appears in the original patent but forms no part of this reissue specification; matter printed in italics indicates the additions made by reissue.

*This application is a reissue of U.S. Pat. No. 6,226,548 issued on May 1, 2001 and also claims benefit under 35 U.S.C. §120 as a continuation of U.S. patent application Ser. No. 10/423,332 filed on Apr. 24, 2003 now RE39,133; which is a reissue of U.S. Pat. No. 6,226,548 issued on May 1, 2001; which claims rights under 35 U.S.C. §119 on provisional application Ser. No. 60/059,915, filed on Sep. 24, 1997. Notice is also given that concurrently filed is United States Patent Application No. filed on; which is also is a reissue of U.S. Pat. No. 6,226,548 issued on May 1, 2001 and also claims benefit under 35 U.S.C. §120 as a continuation of U.S. patent application Ser. No. 10/423,332 filed on Apr. 24, 2003; which is a reissue of U.S. Pat. No. 6,226,548 issued on May 1, 2001; which claims rights under 35 U.S.C. §119 on provisional application Ser. No. 60/059,915, filed on Sep. 24, 1997. The disclosures of the above applications are incorporated herein by reference.*

The present invention claims rights under 35 U.S.C. § 119 on provisional application No. 60/059,915, filed on Sep. 24, 1997, and entitled "Percutaneous Registration Apparatus and Method for Use in Computer-Assisted Surgical Navigation."

FIELD OF THE INVENTION

The present invention relates generally to guiding, directing, or navigating instruments or implants in a body percutaneously, in conjunction with systems that use and generate images during medical and surgical procedures, which images assist in executing the procedures and indicate the relative position of various body parts, surgical implants, and instruments. In particular the invention relates to apparatus and minimally invasive procedures for navigating instruments and providing surgical implants percutaneously in the spine, for example, to stabilize the spine, correct deformity, or enhance fusion in conjunction with a surgical navigation system for generating images during medical and surgical procedures.

BACKGROUND OF THE INVENTION

Typically, spinal surgical procedures used, for example, to provide stabilization, fusion, or to correct deformities, require large incisions and substantial exposure of the spinal areas to permit the placement of surgical implants such as, for example, various forms of screws or hooks linked by rods, wires, or plates into portions of the spine. This standard procedure is invasive and can result in trauma, blood loss, and post operative pain. Alternatively, fluoroscopes have been used to assist in placing screws beneath the skin. In this alternative procedure at least four incisions must be made in the patient's back for inserting rods or wires through previously inserted screws. However, this technique can be difficult in that fluoroscopes only provide two-dimensional images and require the surgeon to rotate the fluoroscope frequently in order to get a mental image of the anatomy in three dimensions. Fluoroscopes also generate radiation to which the patient and surgical staff may become over exposed over time. Additionally, the subcutaneous implants required for this procedure may irritate the patient. A lever arm effect can also occur with the screws that are not connected by the rods or wires at the spine. Fluoroscopic screw placement techniques have traditionally used rods or plates that are subcutaneous to connect screws from vertebra to vertebra. This is due in part to the fact that there is no fluoroscopic technique that has been designed which can always adequately place rods or plates at the submuscular region (or adjacent to the vertebrae). These subcutaneous rods or plates may not be well tolerated by the patient. They also may not provide the optimal mechanical support to the spine because the moment arm of the construct can be increased, thereby translating higher loads and stresses through the construct.

A number of different types of surgical navigation systems have been described that include indications of the positions of medical instruments and patient anatomy used in medical or surgical procedures. For example, U.S. Pat. No. 5,383,454 to Bucholz; PCT Application No. PCT/US94/04530 (Publication No. WO 94/24933) to Bucholz; and PCT Application No. PCT/US95/12894 (Publication No. WO 96/11624) to Bucholz et al., the entire disclosures of which are incorporated herein by reference, disclose systems for use during a medical or surgical procedure using scans generated by a scanner prior to the procedure. Surgical navigation systems typically include tracking means such as, for example, an LED array on the body part, LED emitters on the medical instruments, a digitizer to track the positions of the body part and the instruments, and a display for the position of an instrument used in a medical procedure relative to an image of a body part.

Bucholz et al. WO 96/11624 is of particular interest, in that it identifies special issues associated with surgical navigation in the spine, where there are multiple vertebral bodies that can move with respect to each other. Bucholz et al. describes a procedure for operating on the spine during an open process where, after imaging, the spinous process reference points may move with respect to each other. It also discloses a procedure for modifying and repositioning the image data set to match the actual position of the anatomical elements. When there is an opportunity for anatomical movement, such movement degrades the fidelity of the pre-procedural images in depicting the intra-procedural anatomy. Therefore, additional innovations are desirable to bring image guidance to the parts of the body experiencing anatomical movement.

Furthermore, spinal surgical procedures are typically highly invasive. There is, thus, a need for more minimally invasive techniques for performing these spinal procedures, such as biopsy, spinal fixation, endoscopy, spinal implant insertion, fusion, and insertion of drug delivery systems, by reducing incision size and amount. One such way is to use surgical navigation equipment to perform procedures percutaneously, that is beneath the skin. To do so by means of surgical navigation also requires apparatus that can indicate the position of the spinal elements, such as, for example the vertebrae, involved in the procedure relative to the instruments and implants being inserted beneath the patient's skin and into the patient's spine. Additionally, because the spinal elements naturally move relative to each other, the user requires the ability to reorient these spinal elements to align with earlier scanned images stored in the surgical navigation system computer, to assure the correct location of those elements relative to the instruments and implants being applied or inserted percutaneously.

In light of the foregoing, there is a need in the art for apparatus and minimally invasive procedures for percutaneous placement of surgical implants and instruments in the spine, reducing the size and amount of incisions and utilizing surgical navigation techniques.

SUMMARY OF THE INVENTION

Accordingly, the present invention is directed to apparatus and procedures for percutaneous placement of surgical implants and instruments such as, for example, screws, rods, wires and plates into various body parts using image guided surgery. More specifically, one object of the present invention is directed to apparatus and procedures for the percutaneous placement of surgical implants and instruments into various elements of the spine using image guided surgery.

To achieve these objects and other advantages and in accordance with the purpose of the invention, as embodied and broadly described herein, the invention includes an apparatus for use with a surgical navigation system and comprises an attaching device rigidly connected to a body part, such as the spinous process of a vertebrae, with an identification superstructure rigidly but removably connected to the attaching device. This identification superstructure is a reference arc and fiducial array, which accomplishes the function of identifying the location of the superstructure, and, therefore, the body part to which it is fixed, during imaging by CAT scan or MRI, and later during medical procedures.

In one aspect, the attaching device is a clamp with jaws and sharp teeth for biting into the spinous process.

In another aspect, the fixture is a screw, having a head, wherein the screw is implanted into the spinous process and a relatively rigid wire is attached to the head of the screw and also implanted into the spinous process at an angle to the axis of the screw to prevent the screw from rotating in either direction.

In another aspect, the superstructure includes a central post, and a fiducial array and a reference arc rigidly but removably attached to the central post. The fiducial array is composed of image-compatible materials, and includes fiducials for providing a reference point, indicating the position of the array, which are rigidly attached to the fiducial array, composed of, for example titanium or aluminum spheres. The reference arc includes emitters, such as, for example Light Emitting Diodes ("LEDs"), passive reflective spheres, or other tracking means such as acoustic, magnetic, electromagnetic, radiologic, or micropulsed radar, for indicating the location of the reference arc and, thus, the body part it is attached to, during medical procedures.

In addition, the invention further comprises a method for monitoring the location of an instrument, surgical implants and the various portions of the body, for example, vertebrae, to be operated on in a surgical navigation system comprising the steps of: attaching a fixture to the spinous process; attaching a superstructure including a fiducial array with fiducials and a reference arc to the fixture; scanning the patient using CT, MRI or some other three-dimensional method, with fiducial array rigidly fixed to patient to identify it on the scanned image; and thereafter, in an operating room, using image-guided technology, touching an image-guided surgical pointer or other instrument to one or more of the fiducials on the fiducial array to register the location of the spinal element fixed to the array and emitting an audio, visual, radiologic, magnetic or other detectable signal from the reference arc to an instrument such as, for example, a digitizer or other position-sensing unit, to indicate changes in position of the spinal element during a surgical procedure, and performing a surgical or medical procedure percutaneously on the patient using instruments and implants locatable relative to spinal elements in a known position in the surgical navigation system.

In another aspect, the method includes inserting screws or rigid wires in spinal elements in the area involved in the anticipated surgical procedure before scanning the patient, and after scanning the patient and bringing the patient to the operating area, touching an image-guided or tracked surgical pointer to these screws and wires attached to the vertebrae to positively register their location in the surgical navigation computer, and manipulating either the patient's spine or the image to align the actual position of the spinal elements with the scanned image.

In another aspect, the method includes percutaneously implanting screws into spinal elements, which screws are located using image guided surgical navigation techniques, and further manipulating the orientation of the screw heads percutaneously using a head-positioning probe containing an emitter, that can communicate to the surgical navigation computer the orientation of the screw heads and position them, by use of a specially designed head-positioning tool with an end portion that mates with the heads of the screws and can rotate those screw heads to receive a rod, wire, plate, or other connecting implant. If a rod is being inserted into the screw heads for example, the method further includes tracking the location and position of the rod, percutaneously using a rod inserter having one or more emitters communicating the location and orientation of the rod to the surgical navigation computer.

The objects of the invention are to provide a user, such as a surgeon, with the system and method to track an instrument and surgical implants used in conjunction with a surgical navigation system in such a manner to operate percutaneously on a patient's body parts, such as spinal vertebrae which can move relative to each other.

It is a further object of this invention to provide a system and method to simply and yet positively indicate to the user a change in position of body parts, such as spinal vertebrae segments, from that identified in a stored image scan, such as from an MRI or CAT scan, and provide a method to realign those body parts to correspond with a previously stored image or the image to correspond with the actual current position of the body parts.

It is a further object of this invention to provide a system or method for allowing a fiducial array or reference arc that is removable from a location rigidly fixed to a body part and replaceable back in that precise location.

It is another object of this invention to provide a system and method for positively generating a display of instruments and surgical implants, such as, for example screws and rods, placed percutaneously in a patient using image-guided surgical methods and techniques.

It is another object of this invention for a percutaneous reference array and fiducial array, as described in this appplication, to be used to register and track the position of the vertebrae for the purposes of targeting a radiation dose to a diseased portion of said vertebrae using a traditional radiosurgical technique.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in this description.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate one embodiment of the invention and together with the description, serve to explain the principles of the invention.

DETAILED DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts. The following example is intended to be purely exemplary of the invention.

Figure 1:
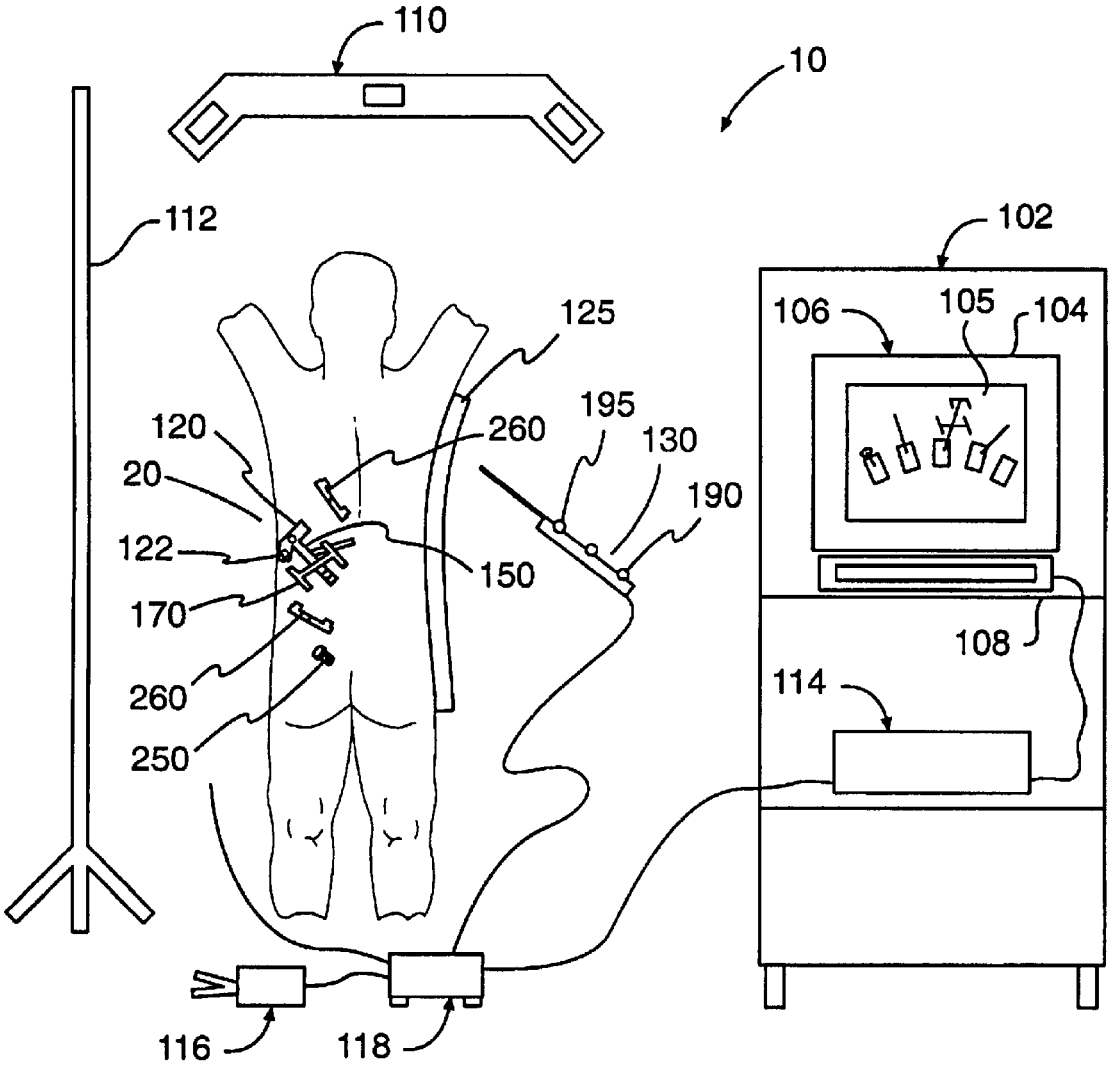
FIG. 1 is a schematic diagram of one preferred embodiment of a superstructure for use in the current invention, including a reference arc, center post and fiducial array and rigid Kirschner wires ("K wires") and screws placed in the spine for use with a surgical navigation system for percutaneous spinal surgical procedures.

As generally described in PCT/US95/12894, the entire disclosure of which is incorporated herein by reference, a typical surgical navigation system is shown in FIG. 1 adopted to be used in the present invention. A computer assisted image-guided surgery system, indicated generally at 10, generates an image for display on a monitor 106 representing the position of one or more body elements, such as spinal elements fixedly held in a stabilizing frame or device such as a spinal surgery frame 125 commonly used for spinal surgery. A reference arc 120 bearing tracking means or emitters, such as for example LED emitters 122, is mounted to the spinous process by a central post 150. The structures 20 and K wires 260 of FIG. 1 are depicted in more detail in FIG. 1A. The image 105 is generated from an image data set, usually generated preoperatively by a CAT scanner or by MRI for example, which image 105 has reference points for at least one body element, such as a spinal element or vertebrae. The reference points of the particular body element have a fixed spatial relation to the particular body element.

The system includes an apparatus such as a digitizer or other Position Sensing Unit (PSU), such as for example sensor array 110 on support 112 for identifying, during the procedure, the relative position of each of the reference points to be displayed by tracking the position of emitters 122 on arc 120. The system also includes a processor 114 such as a PC or other suitable workstation processor associated with controller 108 for modifying the image data set according to the identified relative position of each of the reference points during the procedure, as identified by digitizer 110. The processor 114 can then, for example, generate an image data set representing the position of the body elements during the procedure for display on monitor 106. A surgical instrument 130, such as a probe or drill or other tool, may be included in the system, which is positioned relative to a body part and similarly tracked by sensor array 110.

In summary, the general operation of a surgical navigating system is well known in the art and need not further be described here.

Figure 2:
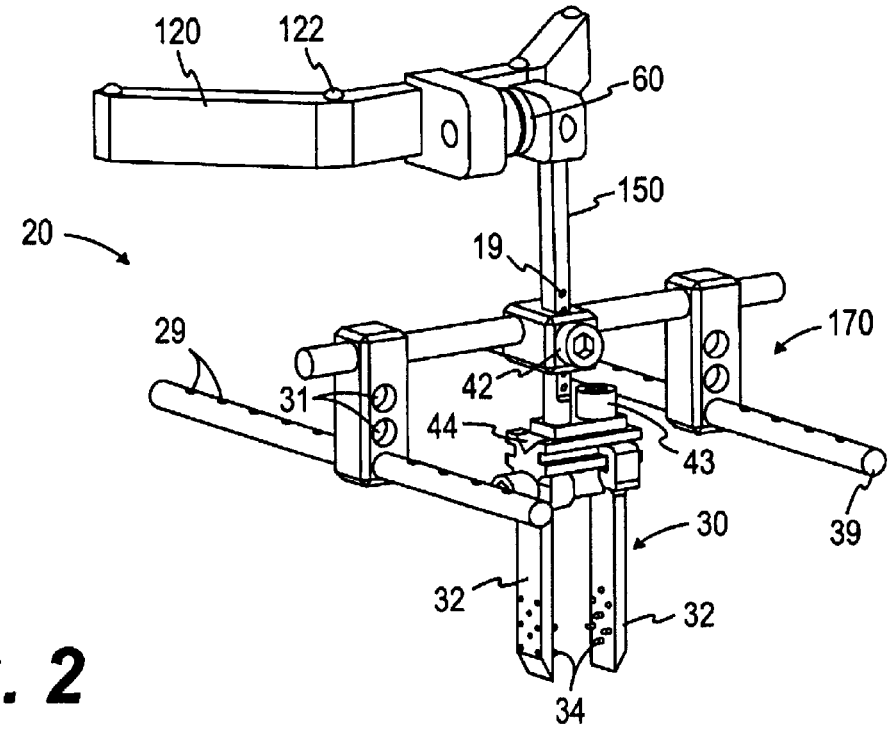
FIG. 2 is a diagram of the preferred embodiment of a clamp fixture for rigid connection to the spinous process of a single vertebrae with an H-shaped fiducial array attached to a center post rigidly attached to the clamp and a mating connector at the tip of the post for mating with a reference array, and a reference array for use in the current invention.
Figure 2A:
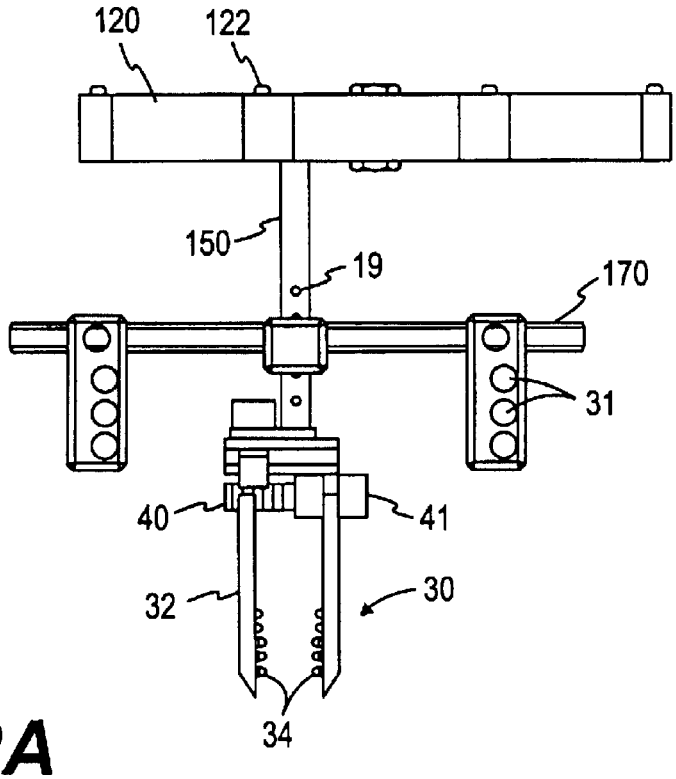
FIG. 2A is a side view of FIG. 2
Figure 2B:
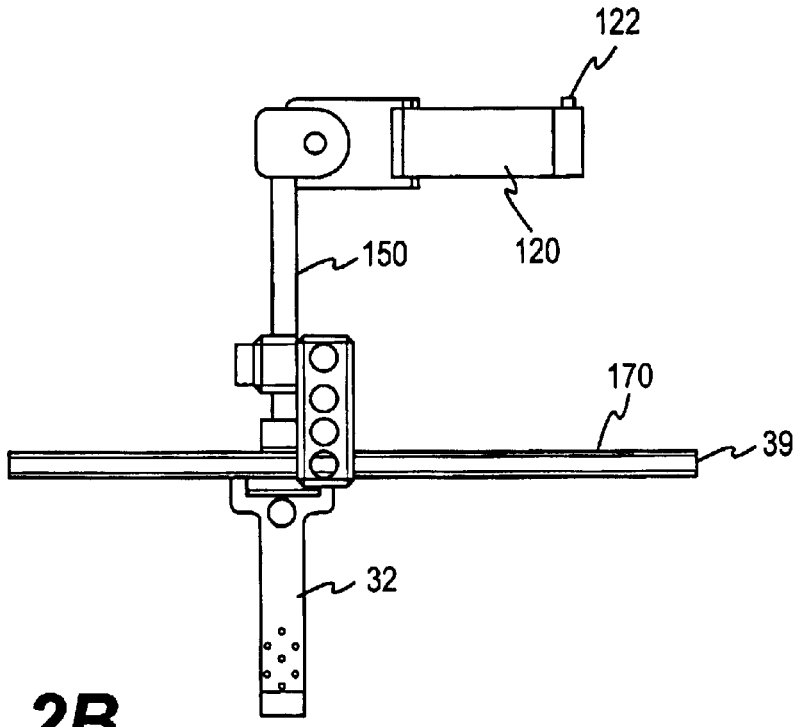
FIG. 2B is another side view of FIG. 2.
Figure 2C:
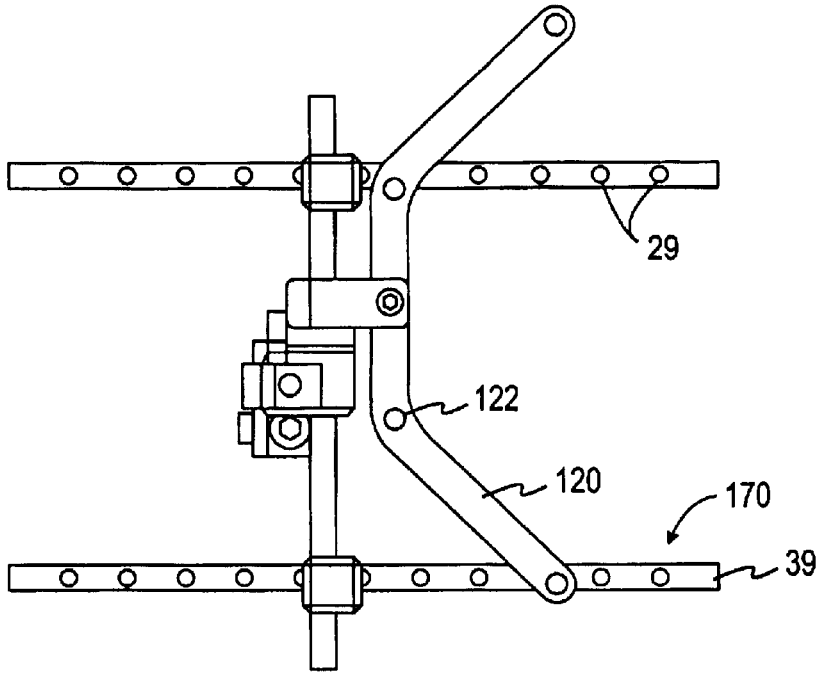
FIG. 2C is a top view of FIG. 2.

In accordance with the preferred embodiment of the present invention, with further reference to FIGS. 1 through 6, a registration device 20 is rigidly fixed to a spinal element by, for example, a device such as a bone clamp 30 depicted in FIG. 2. Alternatively, a screw retention device 40, such as the cannulated screw 42 depicted in FIG. 5, and described in more detail below, can be used.

Figure 1A:
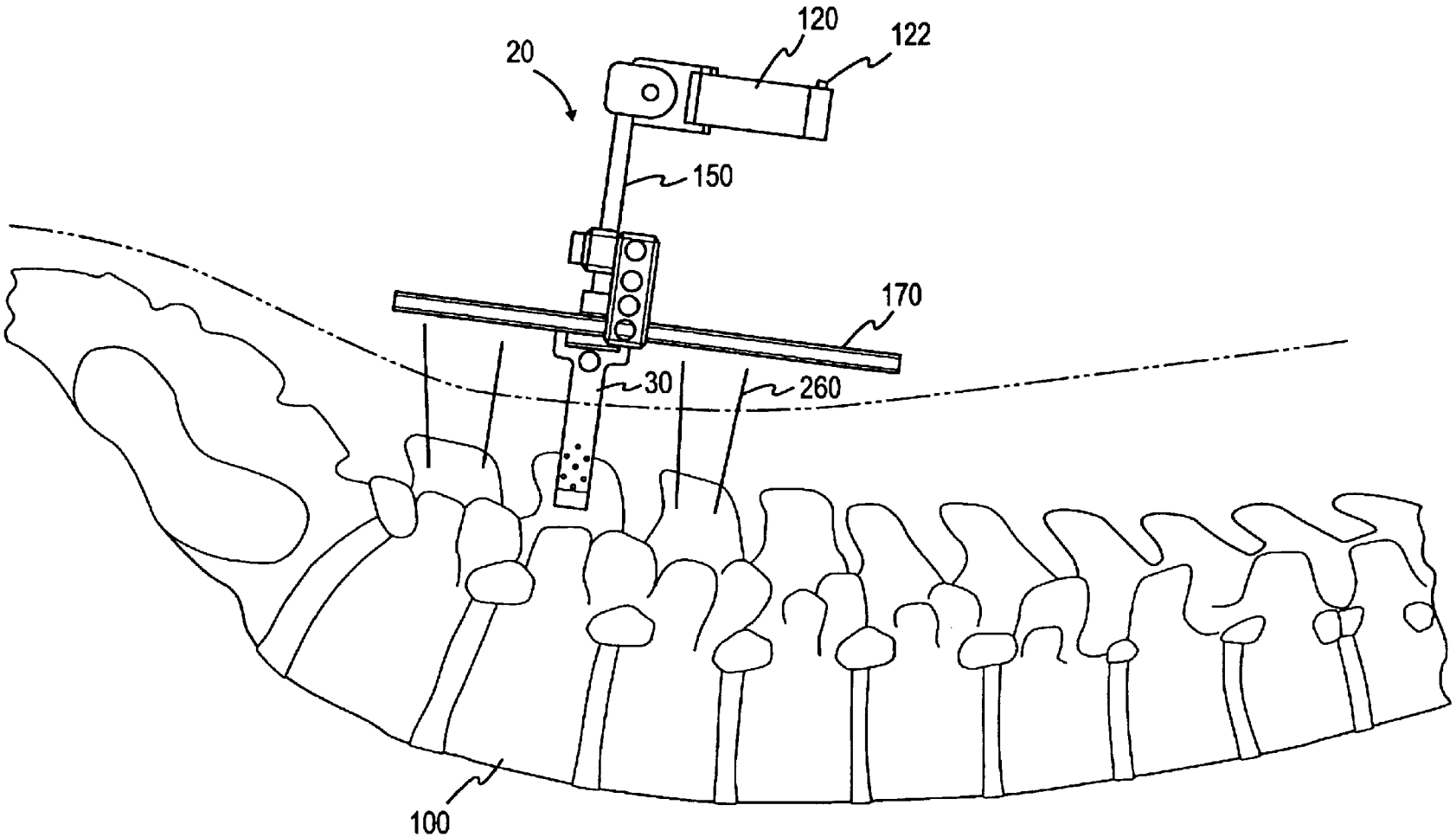
FIG. 1A is an enlarged view of the superstructure depicted in FIG. 1 engaging a vertebra by a clamp and also K wires implanted in adjacent vertebrae in the superior and inferior positions of the spinous process.
Figure 2D:
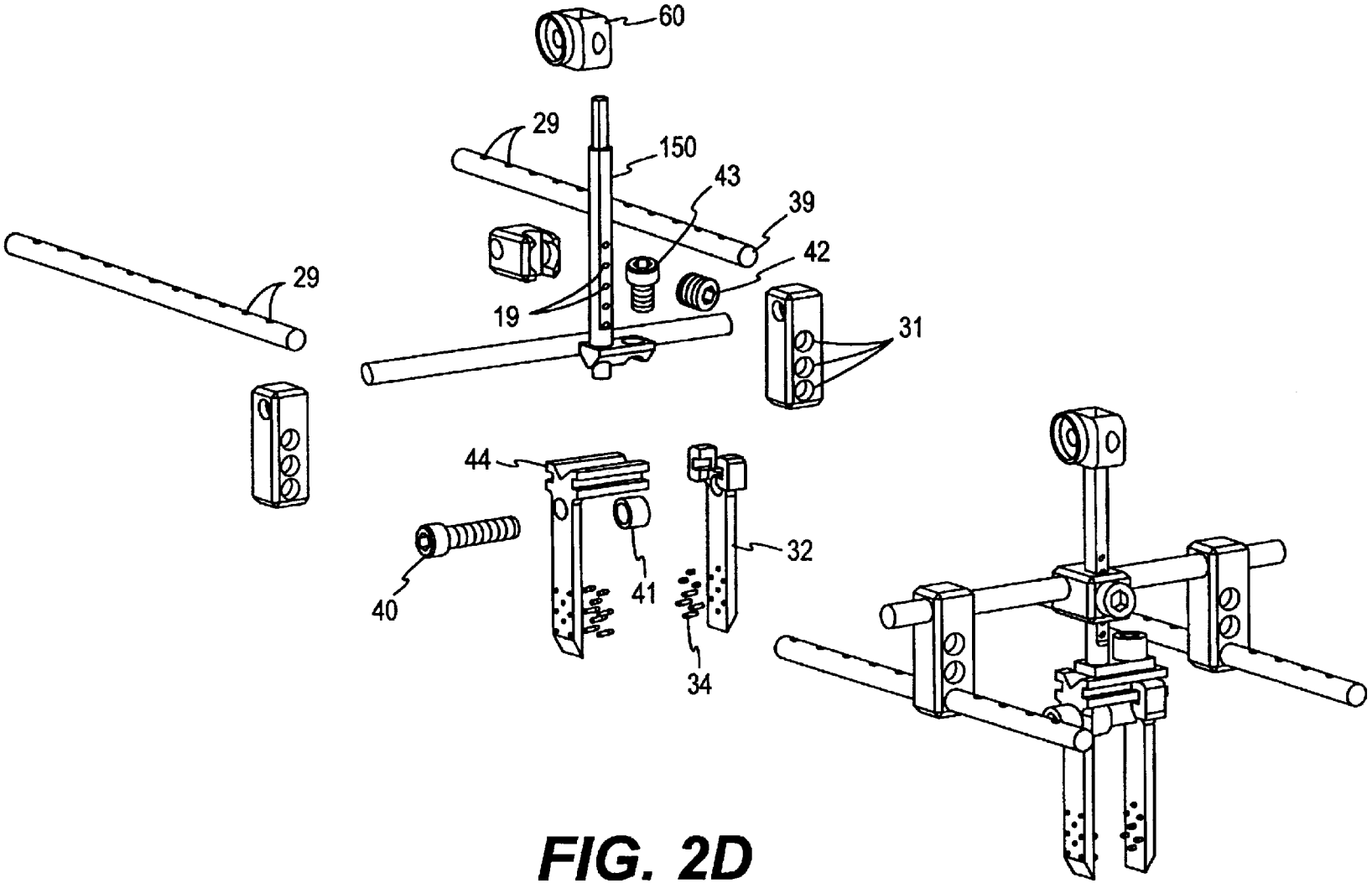
FIG. 2D is an exploded view of FIG. 2 without the reference arc.
Figure 2E:
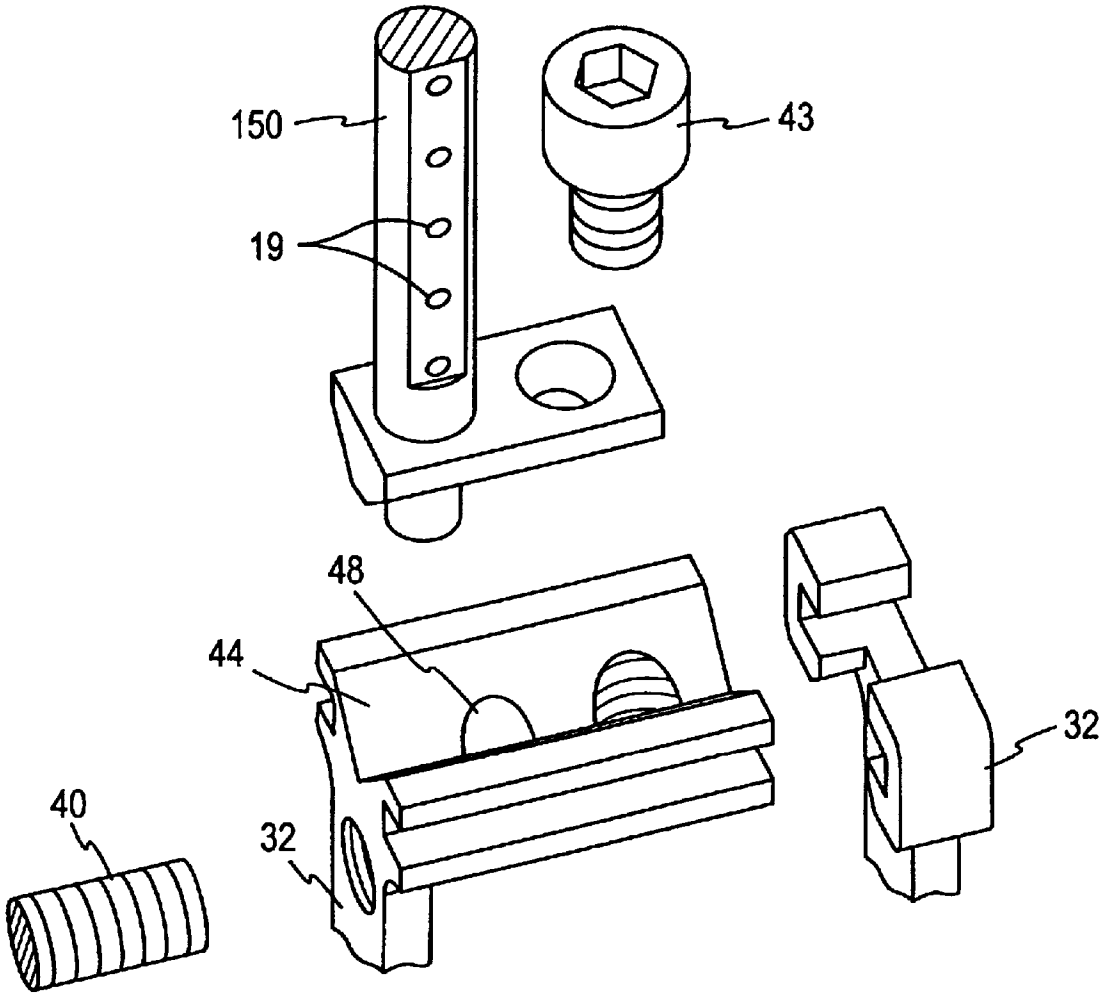
FIG. 2E is an exploded view of the interface of the center post and clamp of FIG. 2.
Figure 11:
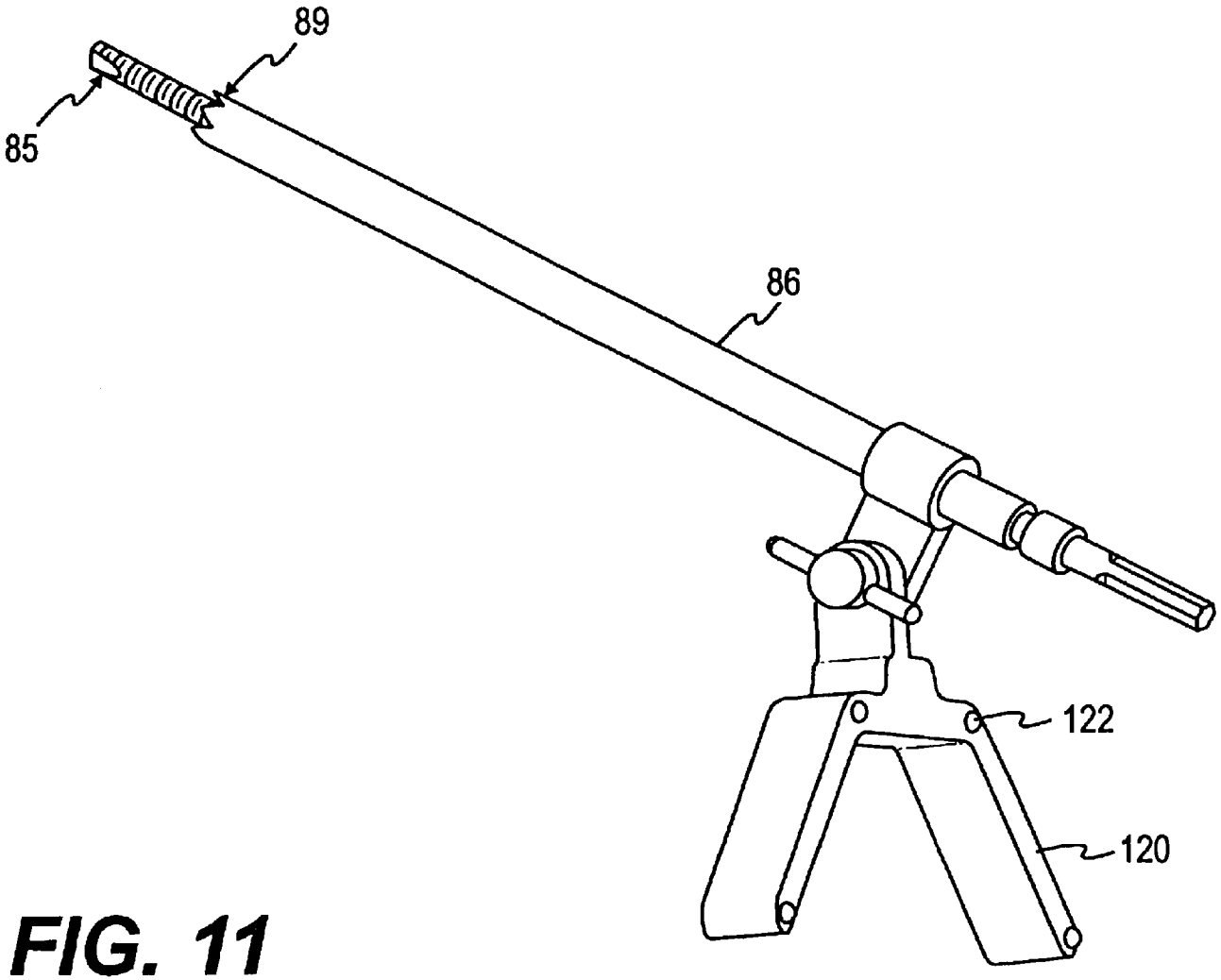
FIG. 11 is a diagram of the cannulated tube of FIG. 10 with a reference arc and screw for attachment to a spinal process.

With reference now to FIG. 2, bone clamp 30 is fixedly attached to the spinous process. The clamp 30 includes at least two blades (or jaws) 32 with tips or teeth 34, which are preferably sharp, for driving together and penetrating soft tissue or more dense bone for rigid fixation to the spinous process. The teeth 34 are also preferably sized to accommodate the bulb shape of the spinous process. The driving mechanism 40 is, for example, a screw driven into a sleeve 41 and is also preferably located such that it will be accessible in a percutaneous manner. Attached to the clamp 30 is a superstructure 20. The superstructure 20 includes a central post 150 which is relocatable, that is, it fixes to the clamp 30 in a rigid fashion, for example, as depicted in FIGS. 2D and 2E, by being inserted into a V-shaped wedge 44 orienting the post 150 front to back and providing a mating hole 48 along the wedge 44 for insertion of post 150 in a single orientation and also providing fasteners such as screw 43 for tightning to lock the post 150 in place. The post 150 can be removed and reapplied by loosening and tightening screw 43, such that the original geometry and orientation is maintained. The central post 150 has at its apex a connector 60 with unique geometrical configuration, such as, for example, a starburst, onto which a spinal reference arc 120 of the superstructure 20 attaches. Any such standard reference arc 120 can be used, such as depicted in FIGS. 1A, 4, and 11, preferably including emitters 122, such as for example LEDs or reflective spheres for providing a positive indication of movement to the surgical navigation system during a procedure.

Figure 3:
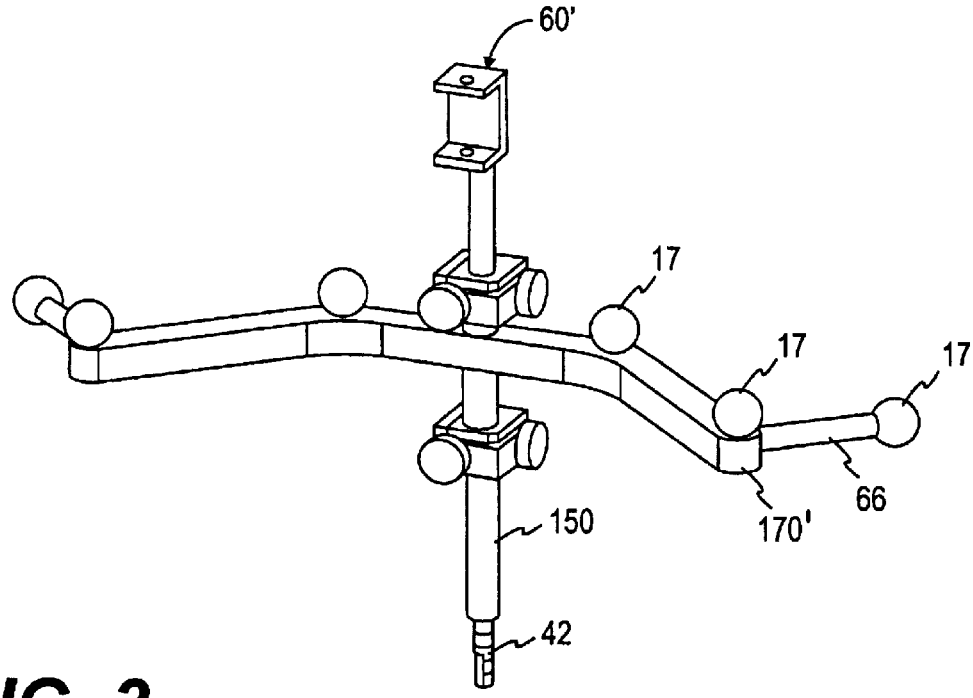
FIG. 3 is a diagram of a W-Shaped fiducial array mounted to a central post with generally spherical fiducials attached to the array, for mounting to a single vertebrae.
Figure 3A:
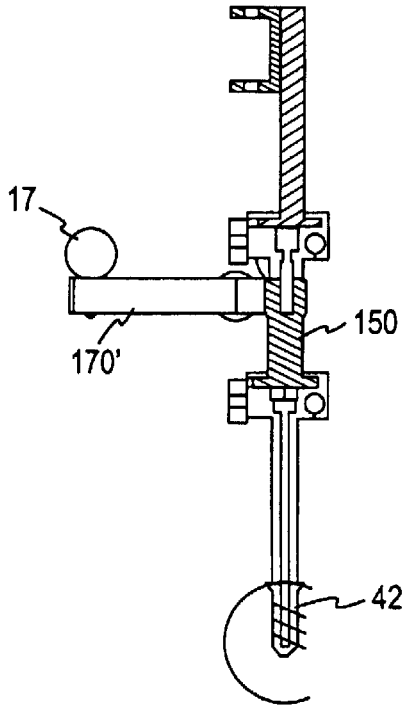
FIG. 3A is a side view of FIG. 3.
Figure 3B:
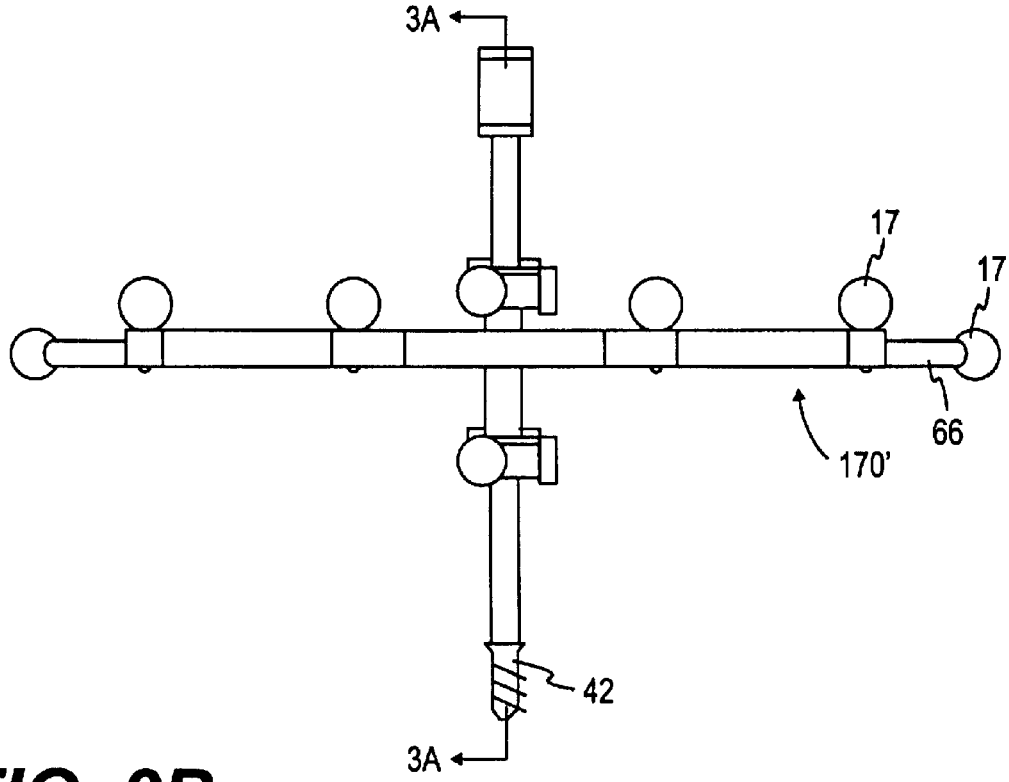
FIG. 3B is another side view of FIG. 3.
Figure 3C:
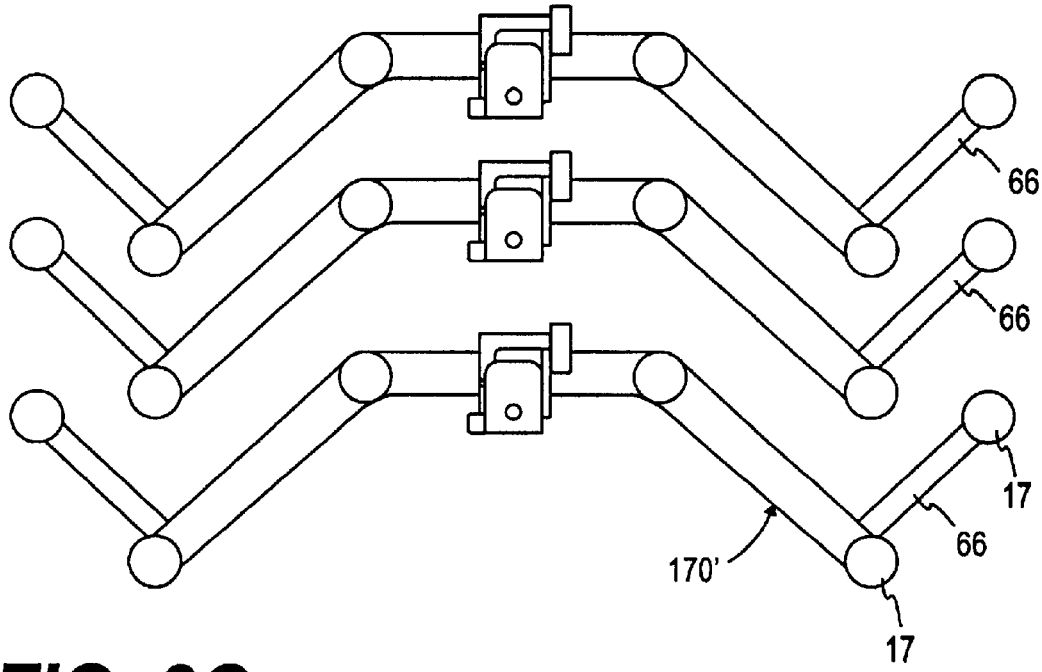
FIG. 3C is a top view of FIG. 3.
Figure 4:
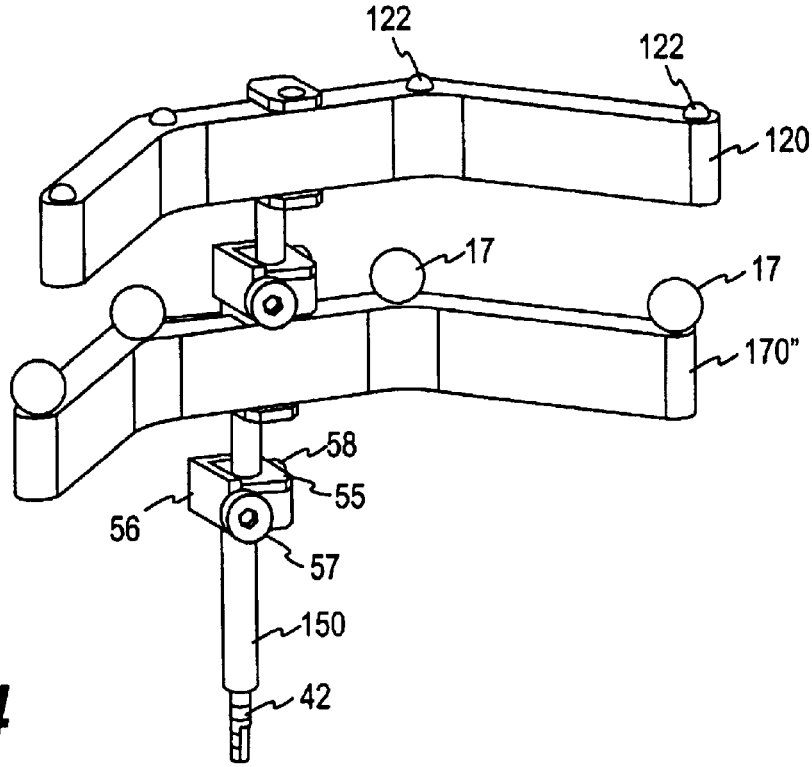
FIG. 4 is a diagram of a reference arc and fiducial attached to a center post for use in the current invention in mounting to a single vertebrae.
Figure 4A:
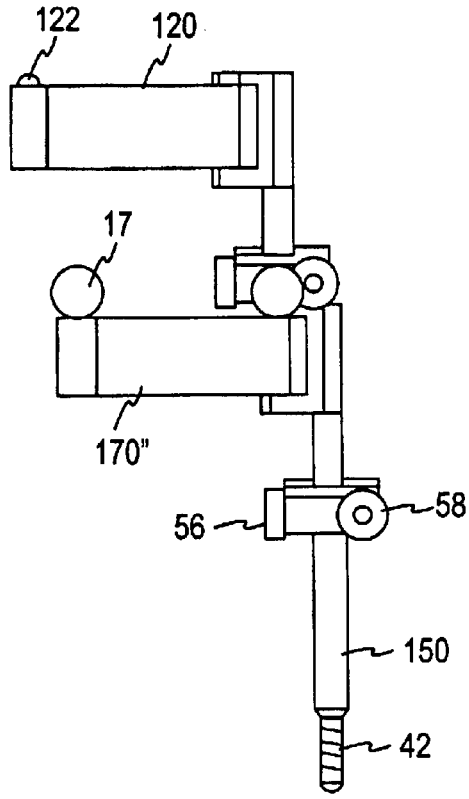
FIG. 4A is a side view of FIG. 4.
Figure 4B:
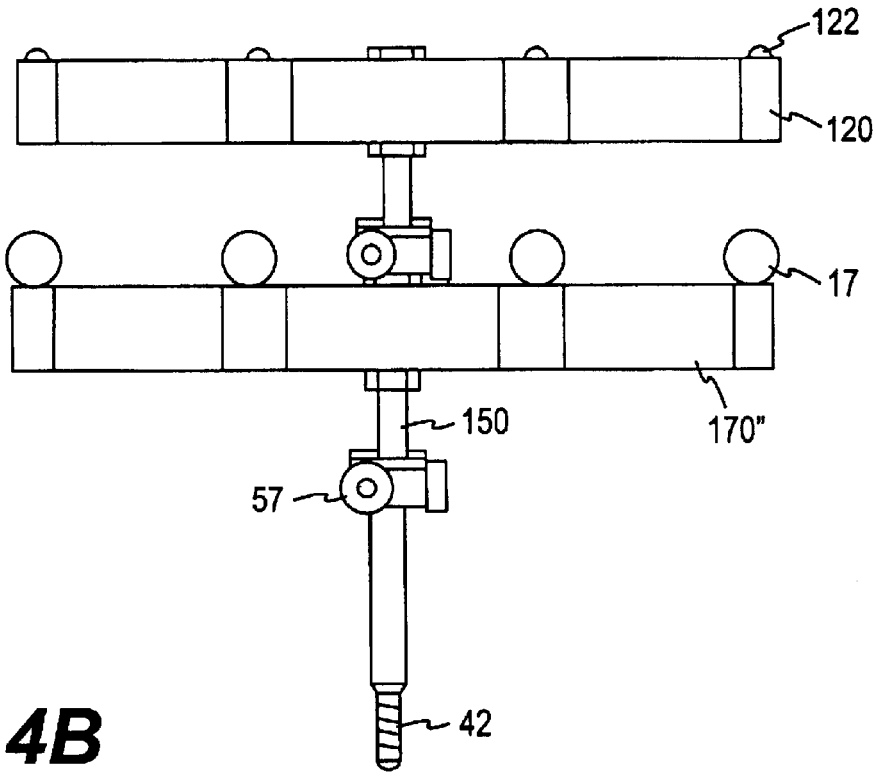
FIG. 4B is a back view of FIG. 4.
Figure 4C:
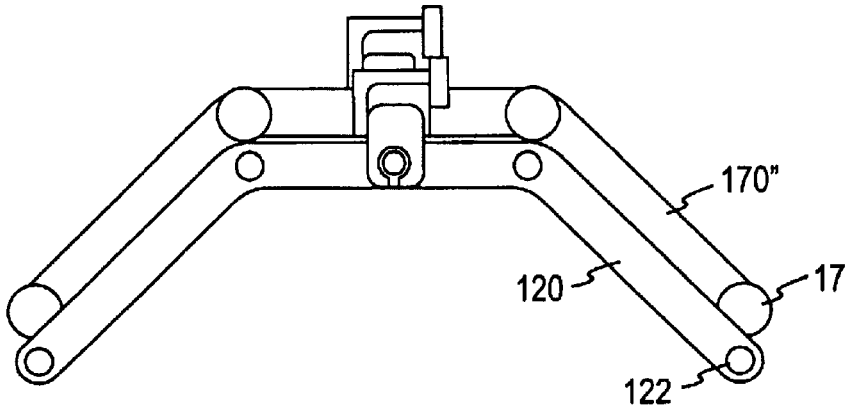
FIG. 4C is a top view of FIG. 4.
Figure 5:
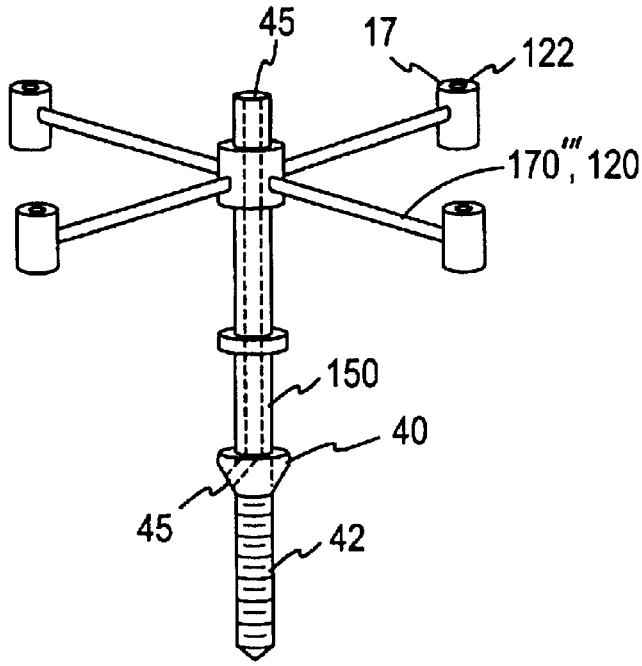
FIG. 5 is a diagram of an alternative embodiment of a fixture for use in the current invention using a cannulated screw for insertion into a vertebrae, with Kirschner wire mounted on a central post and including an alternate embodiment of a fiduciary array and reference arc combined on a single structure.

Also rigidly attached to the central post 150, as part of the superstructure 20 preferably at a location closer to the skin, or possibly collocated with or also performing the function of the reference arc 120, is a fiducial array 170, which can be of various different shapes, such as, for example the H-shaped frame 170 depicted in FIG. 2, the W-shaped frame 170' as depicted in FIG. 3, the U-shaped frame 170" as depicted in FIG. 4 or the X-shaped frame 120', 170'" depicted in FIG. 5 (depicting a structure that is both a fiducial array and a reference arc). As depicted in FIGS. 2 and 3, this array can include fiducial points 29 or spheres 17, rigidly attached to fiducial array 170, 170' and is, for example, as depicted in FIG. 3, substantially in the shape of spheres 17 and of a material detectable by the CAT scan or MRI, preferably titanium or aluminum. This fiducial array such as 170 indicates to the surgical navigation system the location of the bone structure to which the clamp 30 and central post 150 are attached by touching a pointed surgical tracker to fiducial points 29 or a cup-shaped probe to fiducial spheres 17, thereby indicating the center of the fiducial to the surgical navigation controller 114. The array 170 and central post 150 are also attached to the clamp 30, as described above, in such a way that they can be removed and replaced in the same geometric orientation and location, for example, by means of a uniquely shaped interface, for example, a triangle, or a single unique shape or a combination of unique angles or pins with the clamp 30 such that the post 150 can only be reinserted the same way it was removed.

Additionally, the fiducial array 170, can be located at various heights on the post 150 to accomodate variations in patient tissue depth and size, preferably as close to the patient's body as possible, and then fixed at that specific height by the use of pins or indents matched to holes 19 (shown in FIG. 2) in the central post 150 or by placing the rods 39 of H-shaped array 170 in different holes 31. The fiducial array 170 also has, for example, divots 29 (shown in FIG. 2) shaped to interface with an instrument such as a surgical pointer 130 which can touch that divot 29 to register the location of the divot 29 and, thus, the location of the fiducial array 170 and likewise the spinal element in the surgical navigation system. Multiple divots can be registered to further increase accuracy of the registration system. In one preferred embodiment of the array, the fiducials 17 or 29 can be mounted in a manner such that they can be adjusted, for example by mounting them on a rotatable or collapsible arm 66 (as depicted in FIG. 3) that pivots and folds together, to get the maximum distance between fiducials while not dramatically increasing the field of view required at the time of scanning.

Figure 6:
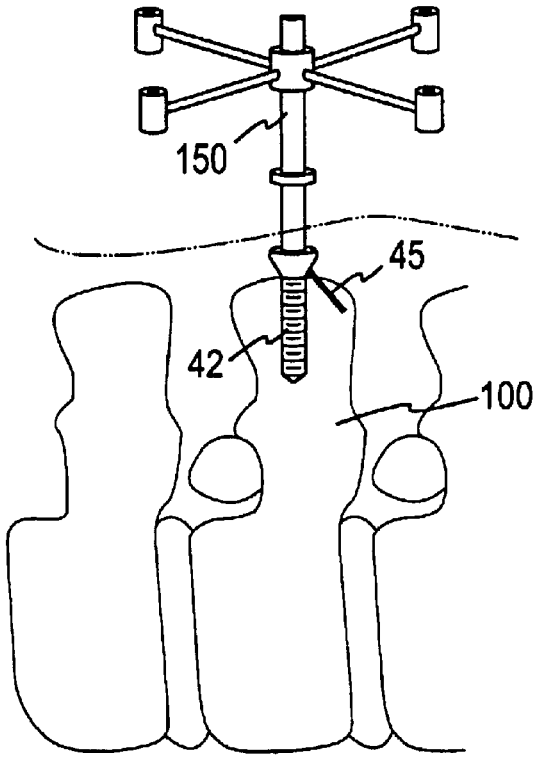
FIG. 6 is a side view of the screw and Kirschner wire fixture of FIG. 5 implanted in a spinous process of a vertebrae.

Alternatively, rather than using clamp 30, a screw 42 and rigid wire 45 attachment, as depicted in FIGS. 5 and 6, may be used to rigidly attach the central post of the superstructure 20 to a body element, such as, for example, a vertebrae. As depicted in FIG. 6, screw 42 is screwed into the spinal process of spinal element 100. A rigid wire 45, post, or other sufficiently rigid fastener such as for example a Kirschner wire (K-wire), is inserted through the cannulation in the center of post 150 and the screw 42 or is otherwise fixed to the screw 42, and exits the tip of the screw 42 at some angle, and is also implanted into the spinal element 100 to prevent the screw 42 from rotating in either direction.

Figure 10:
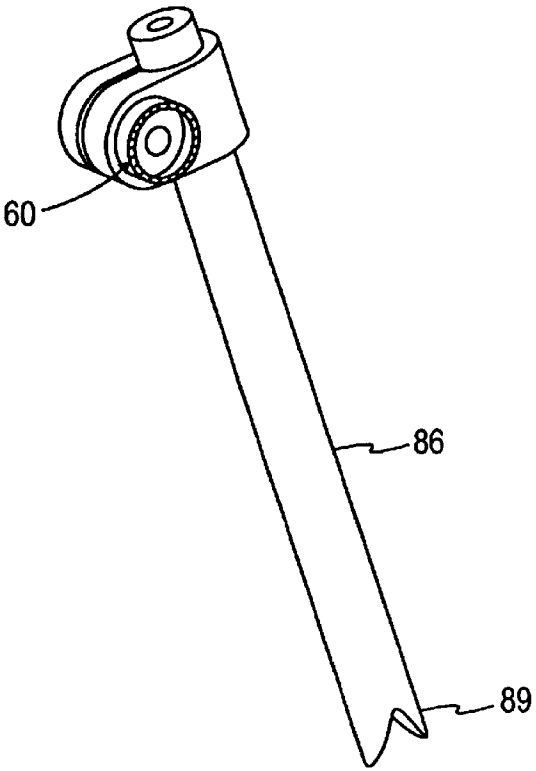
FIG. 10 is a diagram of an alternative embodiment of the invention depicting a cannulated tube and attachment for holding a reference arc.

Another embodiment for preventing the superstructure 20 from rotating as depicted in FIGS. 10 and 11 includes the insertion of a screw 85 through a cannulated tube 86 which has teeth 89 in the end (or V-shaped end) that would bite into the tip of the spinous process, preventing rotation.

Having described the preferred embodiment of this apparatus of the present system, the method of using this apparatus to practice the invention of registering a single vertebrae will now be discussed. The operation of a surgical navigating system is generally well known and is described in PCT/US95/12894. In the preferred method of operation, clamp 30 of FIG. 2 or screw 42 and K-Wire 45 of FIG. 5 are implanted percutaneously through a small incision in the skin and rigidly attached to the spinal process. This attachment occurs with the clamp 30, by driving the blades 32 of the clamp 30 together to hold the spinous process rigidly. The central post 150 is then rigidly fixed to the clamp 30 or screw 42 and the fiducial array 170 is rigidly fixed to the central post 150. The patient is then scanned and imaged with a CAT scan or MRI with a field of view sufficiently large to display the spinal anatomy and the clamp 30 or screw 42 and the fiducial array 170. This scan is loaded into the surgical navigation system processor 104.

Figure 4D:
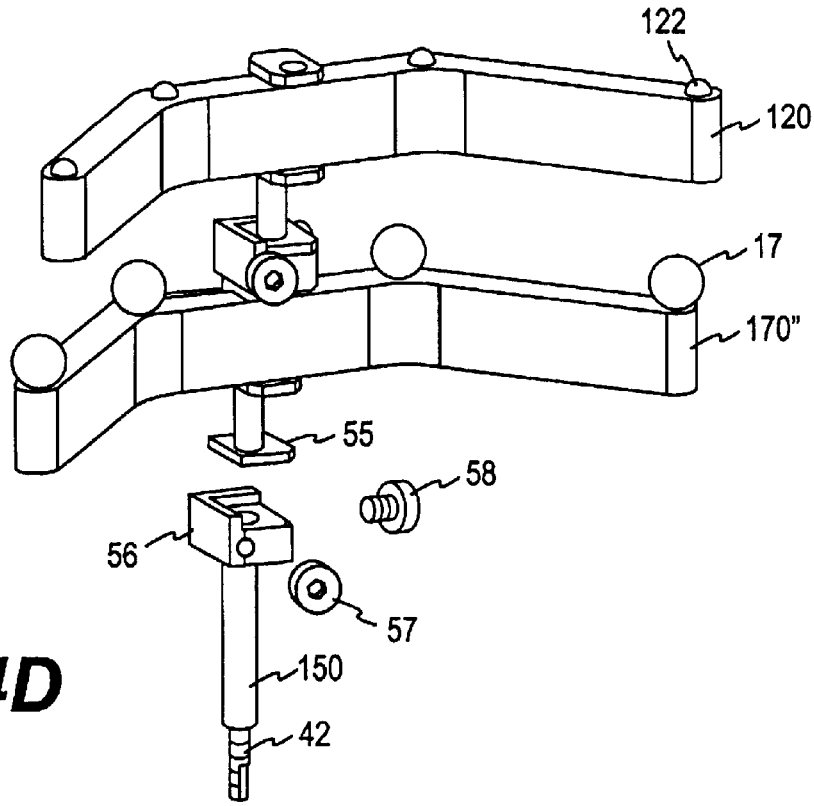
FIG. 4D is an expanded view of FIG. 4.
Figure 4E:
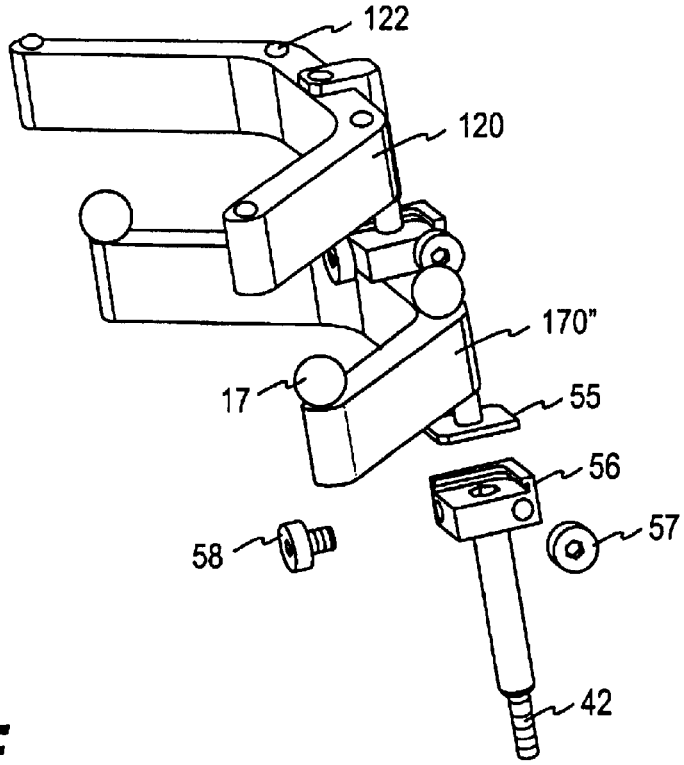
FIG. 4E is an expanded side view of FIG. 4.
Figure 4F:
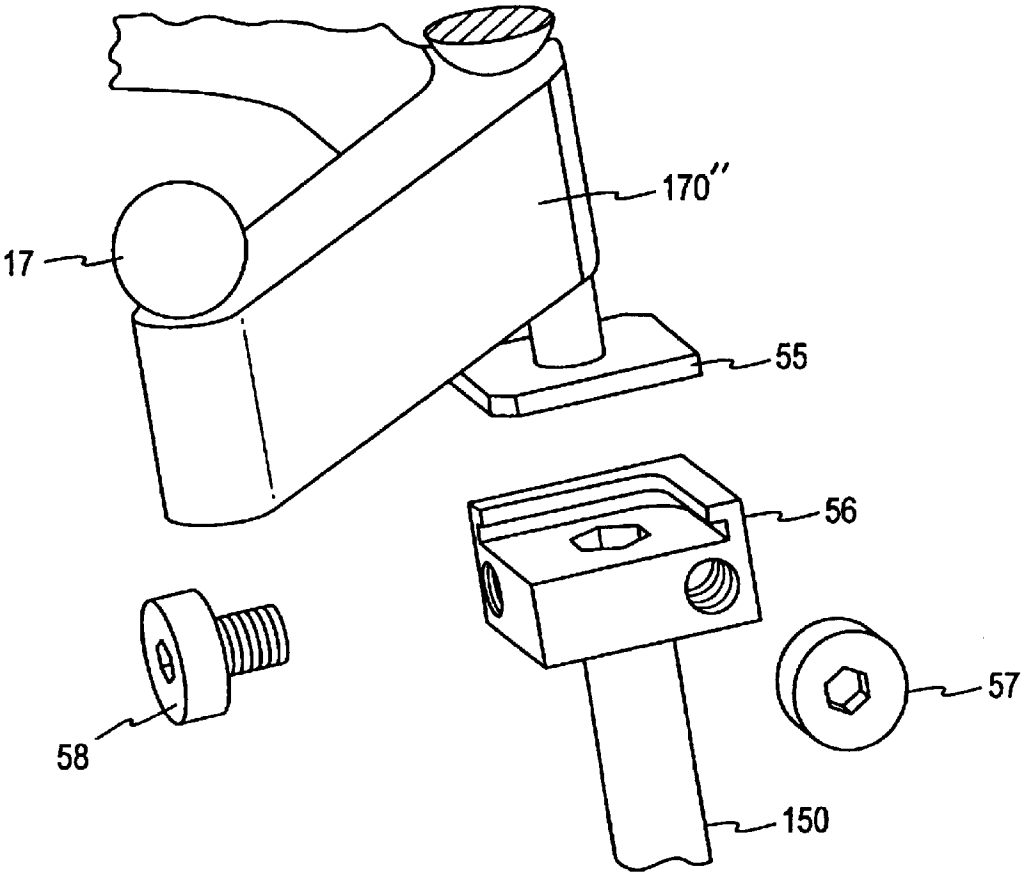
FIG. 4F is an expanded view of the array foot and shoe of FIG. 4E.

After scanning the patient, the array 120 and post 150 can be removed from the patient, while leaving in place the rigidly connected clamp 30 or screw 42. For example, as depicted in FIGS. 4D and 4E, a foot 55 located below array 170" engages with shoe 56 and rigidly connected by screws 57 and 58. Before the surgical procedure, the post 150, array 120 and other remaining portions of the superstructure 20, once removed, may be sterilized. The patient is then moved to the operating room or similar facility from, for example, the scanning room.

Once in the operating room, the patient may be positioned in an apparatus, such as, for example, a spinal surgery frame 125 to help keep the spinal elements in a particular position and relatively motionless. The superstructure 20 is then replaced on the clamp 30 or screw 42 in a precise manner to the same relative position to the spinal elements as it was in the earlier CAT scan or MRI imaging. The reference arc 120 is fixed to the starburst or other interface connector 60 on the central post 150 which is fixed to the clamp 30 or screw 42. The operator, for example a surgeon, then touches an instrument with a tracking emitter such as a surgical pointer 130 with emitters 195 to the divots 29 on the fiducial array 170 to register the location of the array 170 and, thus, because the spinal process is fixed to the fiducial array 170, the location of the spinal element is also registered in the surgical navigation system.

Once the superstructure 20 is placed back on the patient, any instrument 130 fitted with tracking emitters thereon such as, for example, a drill or screw driver, can be tracked in space relative to the spine in the surgical navigation system without further surgical exposure of the spine. The position of the instrument 130 is determined by the user stepping on a foot pedal 116 to begin tracking the emitter array 190. The emitters 195 generate infrared signals to be picked up by camera digitizer array 110 and triangulated to determine the position of the instrument 130. Additionally, other methods may be employed to track reference arcs, pointer probes, and other tracked instruments, such as with reflective spheres, or sound or magnetic emitters, instead of LED's. For example, reflective spheres can reflect infrared light that is emitted from the camera array 110 back to the camera array 110. The relative position of the body part, such as the spinal process is determined in a similar manner, through the use of similar emitters 122 mounted on the reference frame 120 in mechanical communication with the spinal segment. As is well known in this art and described generally in PCT/US95/12894, based upon the relative position of the spinal segment and the instrument 130 (such as by touching a known reference point) the computer would illustrate a preoperative scan—such as the proper CAT scan slice—on the screen of monitor 106 which would indicate the position of the tool 130 and the spinal segment for the area of the spine involved in the medical procedure.

For better access by the operator of various areas near the central post 150, the fiducial array 170 can be removed from the central post 150, by, for example, loosening screw 42 and sliding the array 170 off post 150, leaving the reference arc 120 in place or replacing it after removal of array 170. By leaving the reference arc 120 in place, the registration of the location of the spinal process is maintained. Additionally, the central post 150, reference arc 120, and fiducial array 170 can be removed after the spinal element has been registered leaving only the clamp 30 or screw 42 in place. The entire surgical field can then be sterilized and a sterile post 150 and reference arc 170 fixed to the clamp 30 or screw 42 with the registration maintained.

This surgical navigation system, with spinal element registration maintained, can then be used, for example, to place necessary and desired screws, rods, hooks, plates, wires, and other surgical instruments and implants percutaneously, using image-guided technology. Once the location of the spinal element 100 involved in the procedure is registered, by the process described above, in relation to the image data set and image 105 projected on monitor 106, other instruments 130 and surgical implants can be placed under the patient's skin at locations indicated by the instrument 130 relative to the spinal element 100.

Additionally, the location of other spinal elements, relative to the spinal element 100 containing the fiducial array 170, can be registered in the surgical navigation system by, for example, inserting additional screws 250, rigid wires 260, or other rigid implants or imageable devices into the spinal segment.

Figure 7:
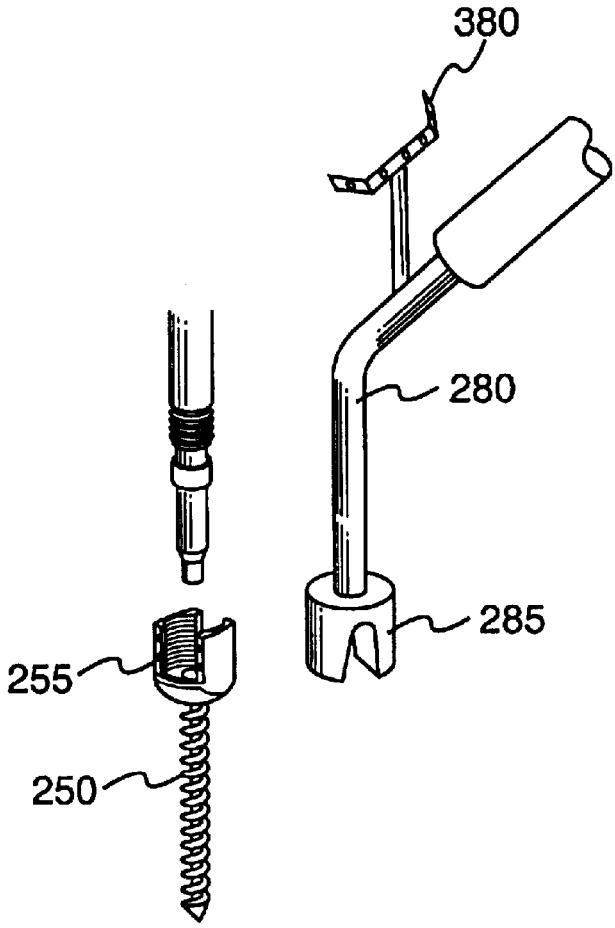
FIG. 7 is a diagram of a screw-head positioning probe and multiaxial screw for insertion into a single vertebrae.
Figure 7A:
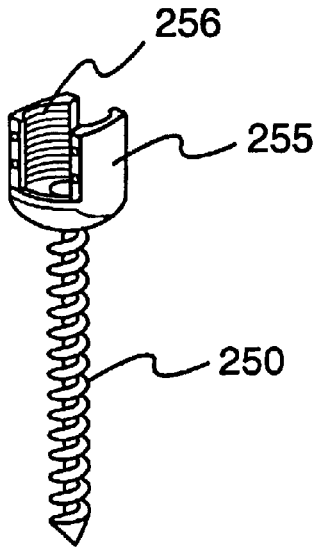
FIG. 7A is a diagram of the screw of FIG. 7.
Figure 8:
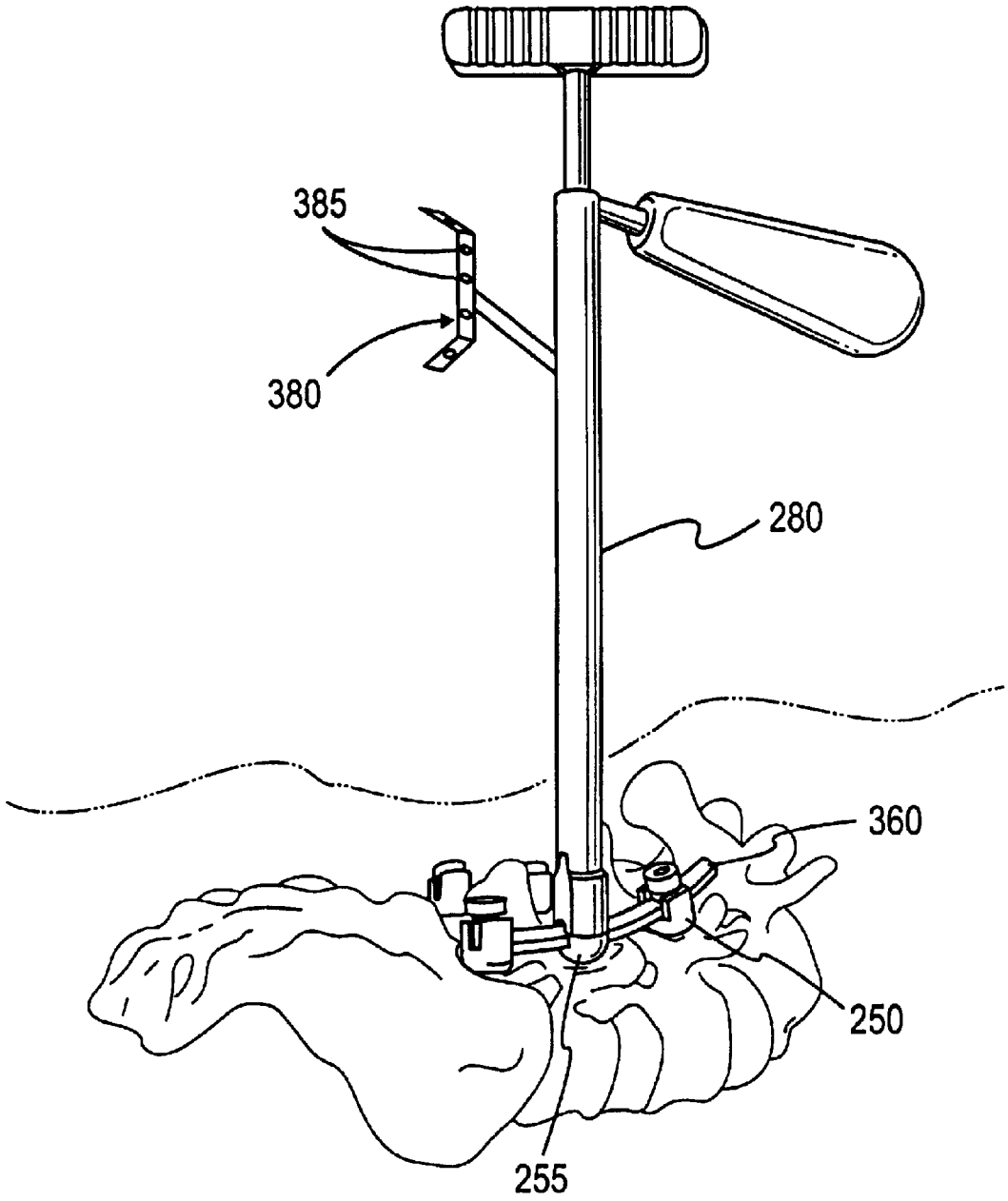
FIG. 8 is a diagram of a head positioning probe, multiaxial screw and spinal segment.

For example, as depicted in FIG. 1, and in more detail FIG. 1A, additional screws 250 or rigid and pointed wires 260 are placed in the vertebrae adjacent to the vertebrae containing the clamp 30 and post 150 prior to scanning. On the image 105 provided by monitor 106, the surgeon can see the clamp 30 or screw 42 and fiducial array 170 and also the additional screws 250, wires 260 or other imageable devices. When screws 250 or other devices are used, these screws 250 (as depicted in FIG. 7) may contain a divot 256 or other specially shaped interface on the head 255 so that a pointer probe 130 can be used to point to the head 255 of the screw 250 (or wire) and indicate the orientation of the screw 250 or wire 260 to the surgical navigation system by communicating to the controller 114 or by emission from LEDs 195 on probe 130 to digitizer 110. The image of these additional screws 250 also appear in the scan. Once the patient is then moved to the operating facility, rather than the scanning area, the image of the screw 250 can be compared to the actual position of the screw 250 as indicated by the pointer probe 130 that is touched to the head 255 of the screw 250 or wire 260. If necessary, the operator can manipulate the position of the patient to move the spinal element and thus the location of the screw 250 or wire 260 to realign the spinal elements with the earlier image of the spine. Alternatively, the operator can manipulate the image to correspond to the current position of the spinal segments.

For additional positioning information, the operator can place additional rigid wires 260 or screws 250 into the vertebrae, for example, located at the superior (toward the patient's head) and inferior (towards the patient's feet) ends of the spinal process to more accurately position those vertebrae relative to the other vertebrae and the image data. Additionally, the wires 260 and screws 250 implanted to provide positioning information can also be equipped with emitters, such as, for example, LEDs, to provide additional information to the surgical navigation system on the location of the wire 260 or screw 250, and thus the vertebra to which they are affixed.

Alternatively, the patient can be placed in a position stabilizing device, such as a spinal surgery frame 125 or board, before a scan is taken, and then moved to the operating facility for the procedure, maintaining the spine segments in the same position from the time of scanning until the time of surgery. Alternatively, a fluoroscope can be used to reposition the spinal segments relative to the earlier image from the scan. An ultrasound probe can be used to take real-time images of the spinal segment which can be portrayed by monitor 106 overlayed or superimposed on image 105. Then the operator can manually manipulate the spinal elements and take additional images of these elements with the fluoroscope to, in an iterative fashion, align the spinal elements with the previously scanned image 105.

Alternatively, a clamp 30 or screw 42 and superstructure 20 can be rigidly fixed to each vertebra involved in the surgical or medical procedure to register the position of each vertebra as explained previously for a single vertebra:

After the spinal elements are registered in the spine, various medical and surgical procedures can be performed on that patient. For example, spinal implants, endoscopes, or biopsy probes can be passed into the spine and procedures such as, for example, spinal fusion, manipulation, or disc removal can be performed percutaneously and facilitated by the surgical navigation image-guiding system. Additionally, a radiation dose can be targeted to a specific region of the vertebrae.

Figure 9:
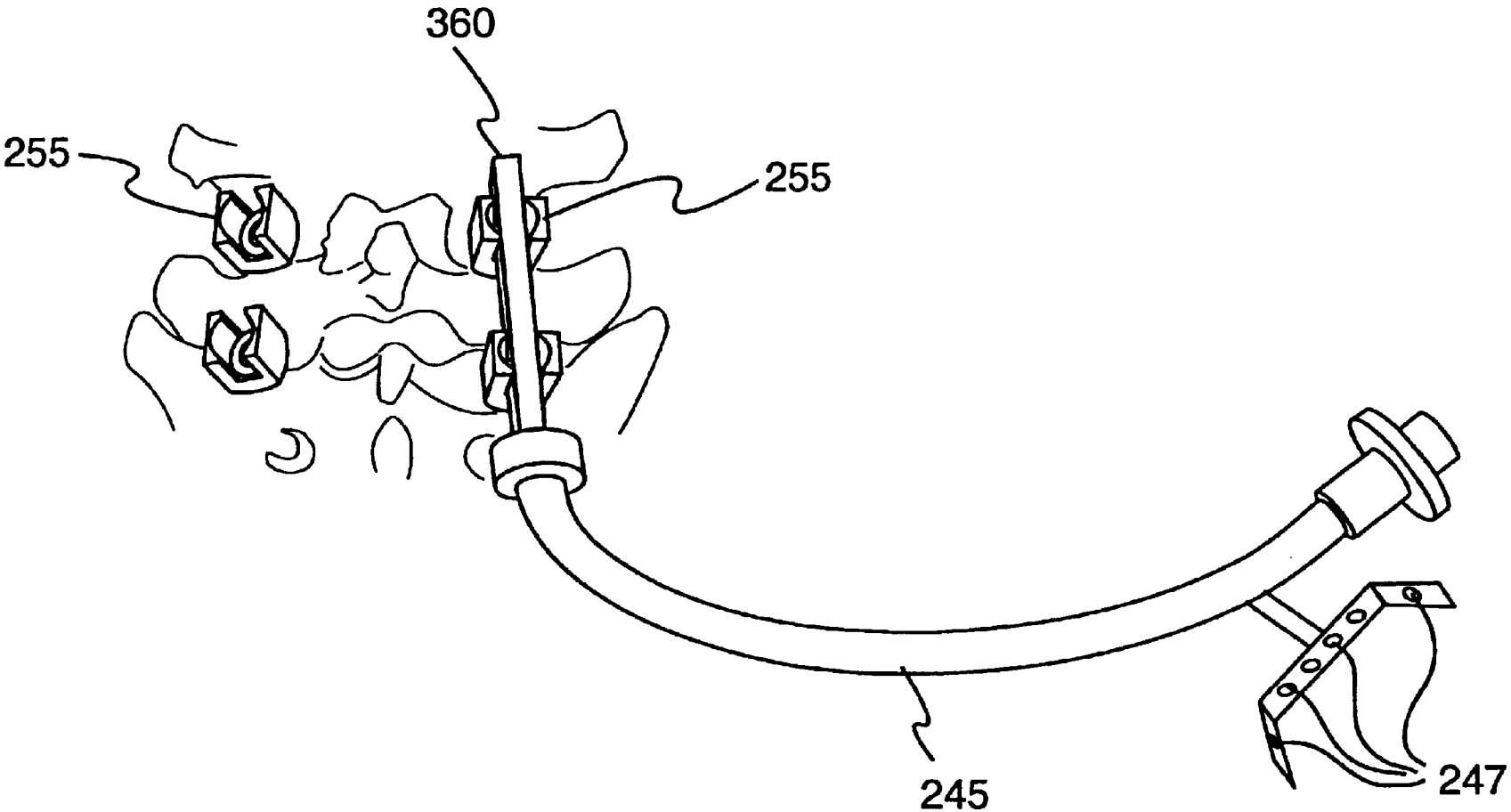
FIG. 9 is a diagram of a rod inserter with an LED.
Figure 12:
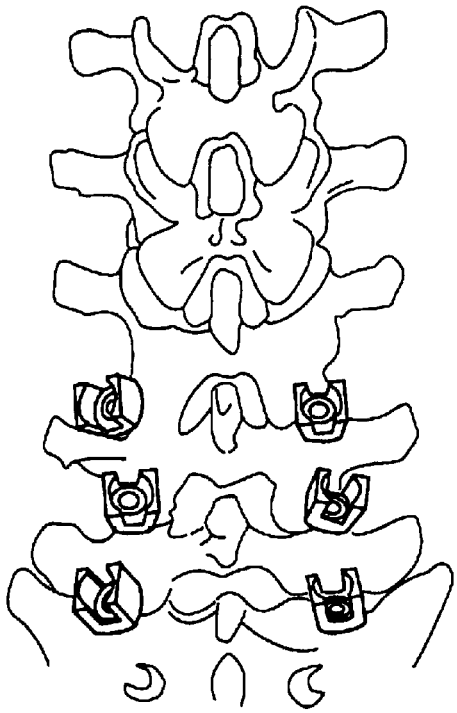
FIG. 12 is a posterior view of spinal segment and implanted screws before alignment.
Figure 13:
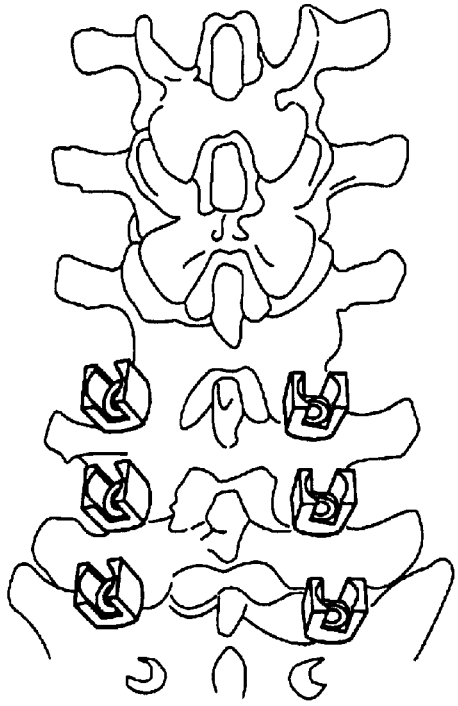
FIG. 13 is a posterior view of spinal segment and implanted screws after alignment.

One such procedure facilitated by the apparatus and methods described above is the percutaneous insertion of screws and rods, fixed to different vertebra in a spine to stabilize them. Once screws, for example multiaxial screws 250, (as depicted in FIG. 12, before manipulation) are implanted through small incisions they can be manipulated by a head-positioning probe 280. The final position of screws 250 and heads 255 are depicted in FIG. 13. This probe 280, as depicted in FIG. 7, includes a head 285 that mates in a geometrically unique fashion with the head 255 of the screw 250. An emitter, such as for example an LED array 380 on the probe 280, indicates the location and orientation of the screw head 255 to the computer 114 of the surgical navigation system by providing an optical signal received by digitizer 110. The screw head 255 can then be rotatably manipulated under the patient's skin by the head positioning probe 280 to be properly oriented for the receipt of a rod 360 inserted through the rotating head 255. The operator can then plan a path from the head 255 of each screw 250 to the other screws 250 to be connected. Then, with reference now to FIG. 9, an optically tracked rod inserter 245 also equipped with emitters, such as, for example LEDs 247, can be placed through another small incision to mate with and guide a rod 360 through the holes or slots in the screw heads 245, through and beneath various tissues of the patient, with the rod inserter 245, and, therefore, the rod 360, fixed to the inserter 245, being tracked in the surgical navigation system. The operator can also use the computer 114 to determine the required bending angles of the rod 360. For greater visualization, the geometry of the screws 250 could be loaded into the computer 114 and when the position and orientation of the head 255 is given to the computer 114 via the probe 280, the computer 114 could place this geometry onto the image data and three-dimensional model. The rod 360 geometry could also be loaded into the computer 114 and could be visible and shown in real time on monitor 106 as the operator is placing it in the screw heads 255.

In an alternative procedure, one or more plates and/or one or more wires may be inserted instead of one or more rods 360.

It will be apparent to those skilled in the art that various modifications and variations can be made in the present invention and in construction of this surgical navigation system without departing from the scope or spirit of the invention. Other embodiments of the invention will be apparent to those skilled in the art from consideration of the specification and practice of the invention disclosed herein. It is intended that the specification and examples be considered as exemplary only.

What is claimed is:

[1. An apparatus for facilitating percutaneous placement of surgical instruments into the spine, adapted for use with a surgical navigation system employing an energy-detecting array in communication with a surgical navigation computer to track positions of instruments in three dimensional space relative to a known reference point, said apparatus comprising:

a connector adapted to be rigidly attached to a portion of the spine;

at least one central post connected to said connector;

a position identification structure rigidly and removably connected to said central post at a predetermined position on said central post and adapted to be reconnected at the same said predetermined position, said identification structure being further adapted to allow a patient to be scanned with the structure connected to the central post, said structure including an assembly for communicating positioning information with respect to said assembly to the energy detecting array and surgical navigation computer; and a connector assembly for said reconnecting of said structure substantially to said predetermined position on said central post.]

[2. The apparatus of claim 1, wherein the connector is a clamp having teeth adapted for biting into a spinous process.]

[3. The apparatus of claim 1, wherein the connector includes an elongated fixture with a central axis and a threaded end adapted to be inserted into the spinous process and a substantially rigid wire connected to the fixture with the central axis of the wire adapted to be implanted into the spinous process at an angle to elongated fixture to prevent the fixture from rotating.]

[4. The apparatus of claim 1, wherein said assembly for communication positioning information is a substantially H-shaped frame.]

[5. The apparatus of claim 1, wherein said assembly for communicating positioning information is a substantially W-shaped frame.]

[6. The apparatus of claim 1, wherein said assembly for communicating positioning information is a substantially U-shaped frame.]

[7. The apparatus of claim 1, wherein said assembly for communicating positioning information is a substantially X-shaped frame.]

[8. The apparatus of claim 1, wherein said assembly for communicating positioning information comprises:

a fiducial array for registering the location of a spinal element with rigidly connected fiducials; and a reference arc for signaling the position of a spinal element, said arc further comprising rigidly connected emitters.]

[9. The apparatus of claim 1, wherein said reference point is on the spine.]

[10. A method for monitoring the location of an instrument, surgical implant and various portions of the body, to be operated on, using a surgical navigation system with a surgical navigation computer and a digitizer array for monitoring the location of instruments in three-dimensional space relative to a known reference point, said method comprising the steps of:

attaching a fixture having a central post to a portion of the spine;

removably attaching an identification structure including a fiducial array and a reference arc to said central post;

providing a scanned three-dimensional image of a patient including said fiducial array rigidly attached to said central post of said fixture, said fixture being rigidly attached to the patient to identify the position of said fixture and said fiducial array on the scanned image;

using an image-guided system, by touching an image guided surgical pointer to one or more fiducials on the fiducial array to register the location of a spinal element fixed to said array; and emitting a signal from said reference arc to indicate changes in position of the spinal element during a surgical procedure.]

[11. The method of claim 10, further comprising:

performing a surgical procedure percutaneously on a patient using an instrument and implant locatable relative to the spinal element and said structure in known positions identified in the surgical navigation system.]

[12. The method of claim 10, further comprising:

inserting a threaded fixture having a substantially rigid wire into a spinal element; and touching an image guided pointer to said threaded fixture and wire to positively register the location of said fixture and wire in a surgical navigation computer.]

[13. The method of claim 10, further comprising:

implanting imageable devices into spinal elements to identify the location of the spinal elements in the surgical navigation computer.]

[14. The method of claim 10, further comprising:

implanting imageable devices into a plurality of spinal elements; and manipulating the patient's spine by viewing the location of the implanted devices, as communicated to the surgical navigation computer by touching an instrument with a tracking emitter to said implanted imageable devices to align the actual position of the spinal elements with the previously scanned image.]

[15. The method of claim 10 further comprising:

percutaneously implanting screws into spinal elements; and locating the position of said screws using image guided surgical navigation techniques.]

[16. The method of claim 15 further comprising:

manipulating the orientation of the screw heads percutaneously using a head-positioning probe for communicating location containing an emitter, said probe communicating to the surgical navigation computer the orientation of the screw heads; and using a head positioning tool for manipulating implants having an end portion that mates with the heads of the screws and rotating the screws to receive a connecting implant.]

[17. The method of claim 16 further comprising:

tracking the location and position of the connecting implant by means of an instrument affixed to the implant having emitters capable of communicating orientation and location to the surgical navigation computer.]

[18. A system for use in performing the percutaneous placement of surgical implants and instruments into the spine using image guided surgery and a surgical navigation computer and energy detecting array, said system comprising:

means for attaching a fixture to a portion of the spine;

means for communicating position information to the surgical navigation computer and energy detecting array said means rigidly and removably connected to said means for attaching a fixture;

means for providing location information of said spinal portion to the surgical navigation system adapted to be connected to spinal elements;

means for indicating screw-head position said means electrically connected to the surgical navigation system and adapted to mate with the head of a screw implanted in one or more of said spinal elements.]

[19. The system of claim 18 further comprising:

an elongated implant adapted to be inserted into said implanted screws;

means for indicating the position of said elongated implant electrically connected to the surgical navigation system and adapted to mate with the elongated implant.]

[20. The system of claim 18, wherein said implanted screws have heads and the elongated implant is a rod adapted to be guided through holes in said implanted screw heads.]

*21. A method of positioning an implant in an anatomy, including a first implant portion and a second implant portion with a surgical navigation system, comprising:*

*positioning the first implant portion through an opening in a soft tissue of the anatomy;*

*tracking a position of the first implant portion;*

*interconnecting an implant inserter with the second implant portion;*

*determining a location of the second implant portion; and*

*moving the second implant portion relative to the first implant portion via determining a location of the second implant portion.*

*22. The method of claim 21, wherein positioning a first implant portion through an opening in a soft tissue, moving the second implant portion relative to the first implant portion, or combinations thereof includes positioning the first implant portion, the second implant portion, or combinations thereof percutaneously.*

*23. The method of claim 22, wherein tracking a position of the first implant portion includes;*

*interconnecting a tracking apparatus with the first implant portion; and*

*tracking the tracking apparatus interconnected to the first implant portion.*

*24. The method of claim 23, further comprising:*

*determining a position of the portion of the first implant portion;*

*wherein moving the second implant portion relative to the first implant portion includes determining a location of a second implant portion relative to the first implant portion.*

*25. The method of claim 24, further comprising:*

*displaying the determined position of the first implant portion and the position of the second implant portion.*

*26. The method of claim 21, further comprising:*

*configuring the second implant portion based upon a tracked position of the first implant portion, a determined location of the second implant portion, or combinations thereof.*

*27. The method of claim 21, further comprising:*

*interconnecting a reference frame with the anatomy.*

*28. The method of claim 27, further comprising:*

*displaying a determined position of the second implant portion on a display relative to a registered image of the anatomy.*

*29. The method of claim 21, further comprising:*

*interconnecting a tracking apparatus with the implant inserter; and*

*tracking the tracking apparatus.*

*30. The method of claim 29, wherein the tracking apparatus includes a sensor.*

*31. The method of claim 30, further comprising:*

*selecting a sensor to include at least one of a light emitter, an infrared light emitter, an electromagnet, a magnet, a radiation emitter, an acoustic emitter, or combinations thereof.*

*32. The method of claim 21, wherein determining a location of the second implant further includes tracking the tracking apparatus.*

*33. The method of claim 21, further comprising:*

*imaging the anatomy while at least one of tracking the position of the first implant, tracking the tracking apparatus, determining a location of a portion of the second implant portion, or combinations thereof.*

*34. The method of claim 33, wherein imaging the anatomy includes imaging the anatomy with an ultrasound system.*

*35. The method of claim 21, further comprising:*

*positioning a third implant portion through an opening in a soft tissue; and*

*interconnecting the first implant portion and the third implant portion with the second implant portion by moving the second implant portion relative to the first implant portion and the third implant portion.*

*36. The method of claim 21, wherein said first implant portion is a slot in a screw head;*

*wherein said second implant portion is a rod;*

*wherein moving the second implant portion includes aligning the rod with the slot.*

*37. The method of claim 36, further comprising:*

*fixing the first implant portion to a vertebrae.*

*38. The method of claim 21, wherein tracking a position includes tracking with an acoustic tracking system, optical tracking system, electromagnetic tracking system, micropulsed radar, or combinations thereof.*

*39. A method of performing a spinal procedure in an anatomy with a surgical navigation system, comprising:*

*positioning a first screw implant in a vertebrae percutaneously through an opening in a soft tissue of the anatomy;*

*tracking a position of the first screw implant with a screw tracking apparatus;*

*orientating the first screw implant in a selected orientation at least in part via tracking the position of the first screw implant;*

*interconnecting an implant inserter with a rod;*

*determining a position of a portion of the rod; and*

*moving the rod relative to the first screw implant via determining a location of the rod to interconnect the screw with rod.*

*40. The method of claim 39, further comprising:*

*interconnecting a second tracking apparatus with the implant inserter.*

*41. The method of claim 39, wherein orientating said first screw implant includes orientating a slot defined by the screw.*

*42. The method of claim 41, wherein tracking a position of the first screw implant includes interconnecting the screw tracking apparatus with the first screw implant.*

*43. The method of claim 42, wherein interconnecting the screw tracking apparatus includes selecting a sensor.*

*44. The method of claim 43, wherein selecting the sensor includes selecting a light emitting diode, a light reflector, an infrared emitter, a magnet, an electromagnet, an acoustic emitter, an infrared reflector, or combinations thereof.*

*45. The method of claim 42, wherein interconnecting the screw tracking apparatus with the first screw implant includes positioning the screw tracking apparatus percutaneously.*

*46. The method of claim 42, wherein tracking the tracking apparatus includes at least triangulating a position of the tracking apparatus with the surgical navigational system.*

*47. The method of claim 46, wherein the surgical navigation system includes an acoustic tracking system, or electromagnetic tracking system, an optical tracking system, a micropulsed radar, or combinations thereof.*

*48. The method of claim 41, wherein orientating the first screw implant includes orientating the slot relative to the anatomy.*

*49. The method of claim 48, further comprising:*

*positioning a second screw implant in a vertebrae percutaneously; and*

*orientating the second screw implant;*

*wherein orientating the second screw implant includes orientating second screw implant relative to the first screw implant.*

*50. The method of claim 49, wherein moving the rod relative to the first screw implant includes moving the rod relative to both the first screw implant and the second screw implant.*

*51. The method of claim 50, further comprising:*

*manipulating the rod to achieve an interconnection of the first screw implant and the second screw implant.*

*52. The method of claim 48, wherein interconnecting the implant inserter with the rod includes interconnecting the implant inserter near a first end of the rod, a second end of the rod, a portion intermediate between the first end and the second end, or combinations thereof.*

*53. The method of claim 48, wherein interconnecting an implant inserter with a rod includes rigidly interconnecting an implant inserter with the rod.*

*54. The method of claim 53, further comprising:*

*interconnecting a tracking apparatus with the implant inserter that includes rigidly interconnecting the tracking apparatus with the implant inserter.*

*55. The method of claim 48, wherein interconnecting an implant inserter with a rod includes releasably interconnecting the implant inserter with the rod.*

*56. The method of claim 48, further comprising:*

*interconnecting a tracking apparatus with the implant inserter that includes positioning an emitter on the tracking apparatus.*

*57. The method of claim 56, wherein interconnecting a sensor with the tracking apparatus includes selecting at least one of a light emitting a diode, a light reflecting portion, an infrared light emitting portion, an infrared light reflecting portion, an acoustic emitter, an electromagnet, a magnet, or combinations thereof.*

*58. The method of claim 48, further comprising:*

*imaging a portion of the anatomy.*

*59. The method of claim 58, wherein imaging an portion of the anatomy includes obtaining an MRI scan, a CT scan, an x-ray image, an ultrasound image, or combinations thereof.*

*60. The method of claim 48, further comprising:*

*displaying an image of the anatomy; and*

*displaying a position of the portion of the screw on the display relative to the image of the anatomy, and displaying a determined position of the rod relative to the image of the anatomy.*

*61. The method of claim 60, wherein moving the rod relative to the screw includes displaying on the display the portion of the rod relative to the position of the head of the screw.*

*62. The method of claim 61, further comprising:*

*manipulating the rod to achieve a selected interconnection of the rod and the screw implant.*

*63. The method of claim 62, wherein manipulating the rod includes bending the rod.*

*64. The method of claim 63, further comprising:*

*positioning a second screw implant in a vertebrae percutaneously; and*

*moving the rod relative to the screw implant and the second screw implant.*

*65. The method of claim 48, wherein moving the rod relative to the screw includes moving the rod substantially percutaneously.*

*66. The method of claim 65, wherein moving the rod substantially percutaneously includes inserting the rod through a substantially single opening in a soft tissue of the anatomy and moving the rod based upon a tracked position of the rod.*

*67. The method of claim 66, wherein tracking a position of the portion of the screw and determining a position of a portion of the rod is substantially percutaneous.*

*68. The method of claim 48, wherein tracking the position of the first screw implant includes tracking a position of a slot defined by the screw.*

*69. The method of claim 68, wherein moving the rod relative to the first screw implant includes moving the rod percutaneously through the slot.*

*70. The method of claim 69, further comprising:*

*positioning a second screw implant in a vertebrae percutaneously through an opening in a soft tissue of the anatomy;*

*tracking a position of the second screw implant; and*

*orientating the second screw implant in a selected orientation at least in part via tracking the position of the second screw implant.*

*71. The method of claim 70, wherein orientating the second screw implant includes aligning a second slot defined by the second screw implant with a first slot defined by the first screw implant at least in part by tracking the position of the first screw implant, tracking the position of the first screw implant, or combinations thereof;*

*wherein moving the rod includes moving the rod through the first slot and the second slot.*

*72. The method of claim 71, further comprising:*

*fixing the rod to the first screw implant and the second screw implant.*

*73. The method of claim 39, wherein orientating the first screw implant includes selecting an orientation of a head of the screw relative to a portion of the anatomy.*

* * * * *

UNITED STATES PATENT AND TRADEMARK OFFICE

CERTIFICATE OF CORRECTION

PATENT NO. : RE42,226 E
APPLICATION NO. : 11/451595
DATED : March 15, 2011
INVENTOR(S) : Kevin T. Foley et al.

It is certified that error appears in the above-identified patent and that said Letters Patent is hereby corrected as shown below:

Column 1, line 32, above the heading, "FIELD OF THE INVENTION" insert: --Notice: More than one reissue application has been filed for the reissue of patent RE42,226. The reissue applications are RE39,133 and RE42,194.--

Signed and Sealed this
Twenty-sixth Day of February, 2013

Teresa Stanek Rea
*Acting Director of the United States Patent and Trademark Office*